(12) United States Patent
Mahajan

(10) Patent No.: US 12,631,653 B2
(45) Date of Patent: May 19, 2026

(54) METHODS FOR DIAGNOSING AND TREATING UVEITIS

(71) Applicant: The Board of Trustees of the Leland Stanford Junior University, Stanford, CA (US)

(72) Inventor: Vinit Mahajan, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1094 days.

(21) Appl. No.: 17/762,594

(22) PCT Filed: Sep. 24, 2020

(86) PCT No.: PCT/US2020/052487
§ 371 (c)(1),
(2) Date: Mar. 22, 2022

(87) PCT Pub. No.: WO2021/061980
PCT Pub. Date: Apr. 1, 2021

(65) Prior Publication Data
US 2022/0404373 A1 Dec. 22, 2022

Related U.S. Application Data

(60) Provisional application No. 62/905,913, filed on Sep. 25, 2019.

(51) Int. Cl.
G01N 33/68 (2006.01)
A61P 27/02 (2006.01)

(52) U.S. Cl.
CPC .......... G01N 33/6893 (2013.01); A61P 27/02 (2018.01); G01N 2800/16 (2013.01); G01N 2800/52 (2013.01)

(58) Field of Classification Search
None
See application file for complete search history.

(56) References Cited

U.S. PATENT DOCUMENTS

| | | | |
|---|---|---|---|
| 2011/0212104 A1 | 9/2011 | Beaumont et al. | |
| 2015/0141273 A1* | 5/2015 | Bosch ................ | G01N 33/6848 |
| | | | 435/7.92 |
| 2016/0067357 A1 | 3/2016 | Francois et al. | |
| 2017/0058348 A1 | 3/2017 | Stuhlmüller et al. | |

FOREIGN PATENT DOCUMENTS

| | | | |
|---|---|---|---|
| WO | 2019055509 A1 | 3/2019 | |
| WO | WO 2019/122538 | * 6/2019 ............ | G01N 33/68 |

OTHER PUBLICATIONS

Hofmaier et al., Invest Ophthalmol Vis Sci. 2011; 52:2314-2320; DOI: 10.1167/iovs.10-6475 (Year: 2011).*
Wang et al., Scientific Reports, 6:36140; DOI: 10.1038/srep36140 (Year: 2016).*
Clowers et al. (2013) Investigation of the peptidoglycan sensing molecule, PGLYRP-2, in murine inflammatory uveitis. British Journal of Ophthalmology 97(4):504-510.
Lu et al. (2017) Determination of Genes Related to Uveitis by Utilization of the Random Walk with Restart Algorithm on a Protein-Protein Interaction Network. International Journal of Molecular Sciences18(5):1045.
Khan, (2019) Identifcation of serum biomarkers in patients of exfoliative glaucoma in Scandanavian population.: Autoimmune profiling by microarray technology. Master Degree Project in Systems Biology A2E, University of Skovde, Retrieved from the internet: <URL: https://www.diva-portal.org/smash/get/diva2:1353246/FULLTEXT01.pdf>.
Velez et al. (2018) Personalized Proteomics for Precision Health: Identifying Biomarkers of Vitreoretinal Disease. Transl Vis. Sci. Technol. 7(5):12.

* cited by examiner

*Primary Examiner* — Christina M Borgeest
(74) *Attorney, Agent, or Firm* — Jenny L. Buchbinder; Bozicevic, Field & Francis LLP

(57) ABSTRACT

Compositions, methods, and kits are provided for diagnosing and treating uveitis. In particular, biomarkers have been identified that can be used to distinguish infectious uveitis from noninfectious uveitis, and further discriminate among bacterial, viral, and fungal uveitis. These biomarkers can be used alone or in combination with one or more additional biomarkers or relevant clinical parameters in prognosis, diagnosis, or monitoring treatment of uveitis.

10 Claims, 8 Drawing Sheets

FIG. 2A

Pars Plana

Choroid

RPE

Retina

Cornea

Aqueous

Lens

Vitreous Humor

Ciliary Body

Proteins by Infection Class

Upregulated vs. Control (p < 0.05)

Bacterial

Viral

50

3

11

42

23

16

21

Fungal

METHODS FOR DIAGNOSING AND TREATING UVEITIS

BACKGROUND OF THE INVENTION

Intraocular infections due to bacteria, viruses, fungi, helminths, and parasites (infectious endophthalmitis) are among the most common and visually devasting causes of blindness. Since initial clinical examination cannot determine the cause of intraocular inflammation (uveitis), doctors must wait for laboratory culture to identify a microbial agent. But waiting days to weeks for cultures to grow delays diagnosis and treatment, and frequently results in debilitating visual morbidity and blindness. Thus, there is a critical unmet need to develop rapid and precise diagnostic tools for infectious endophthalmitis.

SUMMARY OF THE INVENTION

Compositions, methods, and kits are provided for diagnosing and treating uveitis. In particular, the inventors have discovered biomarkers that can be used to distinguish infectious uveitis from noninfectious uveitis, and further discriminate among bacterial, viral, and fungal uveitis. These biomarkers can be used alone or in combination with one or more additional biomarkers or relevant clinical parameters in prognosis, diagnosis, or monitoring treatment of uveitis.

Biomarkers that can be used in diagnosing uveitis include, without limitation, peptidoglycan recognition protein 1 (PG-LYRP1), elastase, neutrophil expressed (ELANE), matrix metalloproteinase-9 (MMP9), DNA damage-responsive RNA polymerase-degradation factor (DEF1), S100 calcium binding protein A8 (S100A8), SPARC like 1 protein (SPARCL1), LDL receptor related protein 2 (LRP2), chondromodulin (CNMD), chitotriosidase-1 (CHIT1), myeloperoxidase (MPO), lipocalin 2 (LCN2), lymphocyte cytosolic protein 1 (LCP1), cystatin S (CST4), contactin-1 (CNTN1), 4-hydroxyphenylpyruvate dioxygenase (HPD), multiple inositol polyphosphate phosphatase 1 (MINP1), matrix metallopeptidase 8 (MMP8), cyclase associated actin cytoskeleton regulatory protein 1 (CAP1), and serpin family A member 3 (SERPINA3).

In certain embodiments, a panel of biomarkers is used for diagnosis of uveitis. Biomarker panels of any size can be used in the practice of the subject methods. Biomarker panels for diagnosing uveitis typically comprise at least 3 biomarkers and up to 20 biomarkers, including any number of biomarkers in between, such as 3, 4, 5, 6, 7, 8, 9, 10, 11, 12, 13, 14, 15, 16, 17, 18, 19, or 20 biomarkers. In certain embodiments, a biomarker panel comprising at least 3, or at least 4, or at least 5, or at least 6, or at least 7, or at least 8, or at least 9, or at least 10, or at least 11, or at least 12, or at least 13, or at least 14, or at least 5, or at least 16, or at least 17, or at least 18, or at least 19, or more biomarkers. In some embodiments, the biomarker panel comprises or consists of all of the PGLYRP1, ELANE, MMP9, DEF1, S100A8, SPARCL1, LRP2, CNMD, CHIT1, MPO, LCN2, LCP1, CST4, CNTN1, HPD, MINP1, MMP8, CAP1, and SERPINA3 biomarkers. In some embodiments, the biomarker panel comprises or consists of the PGLYRP1, ELANE, MMP9, DEF1, S100A8, SPARCL1, LRP2, and CNMD biomarkers for distinguishing non-infectious uveitis from infectious uveitis. In some embodiments, the biomarker panel comprises or consists of the CHIT1, MPO, LCN2, and LCP1 biomarkers for diagnosing bacterial uveitis. In some embodiments, the biomarker panel comprises or consists of the CST4, CNTN1, HPD, and MINP1 biomarkers for diagnosing viral uveitis. In some embodiments, the biomarker panel comprises or consists of the MMP8, CAP1, and SERPINA3 biomarkers for diagnosing fungal uveitis. Although smaller biomarker panels are usually more economical, larger biomarker panels (i.e., greater than 20 biomarkers) have the advantage of providing more detailed information and can also be used in the practice of the subject methods.

In one aspect, a method of diagnosing and treating uveitis in a patient is provided, the method comprising: a) obtaining a vitreous sample from an eye of the patient; b) measuring levels of expression of at least 3 biomarkers selected from the group consisting of PGLYRP1, ELANE, MMP9, DEF1, S100A8, SPARCL1, LRP2, and CNMD in the vitreous sample, wherein increased levels of expression of PGLYRP1, ELANE, MMP9, DEF1, and S100A8 compared to reference value ranges for a vitreous sample from a subject having non-infectious uveitis indicate that the patient has infectious uveitis, and decreased levels of expression of SPARCL1, LRP2, and CNMD compared to reference value ranges for a vitreous sample from a subject having infectious uveitis indicate that the patient has non-infectious uveitis; and c) treating the patient for non-infectious uveitis, if the patient has a positive diagnosis for non-infectious uveitis.

In certain embodiments, the patient is treated for non-infectious uveitis with a glucocorticoid steroid, a cycloplegic agent, an antimetabolite, a T-cell inhibitor, an anti-tumor necrosis factor (TNF) agent, a biologic agent, or an alkylating agent, or a combination thereof. Exemplary glucocorticoid steroids include, without limitation, prednisolone, methylprednisolone, iluvien, ozurdex, retisert, and triamcinolone. Exemplary T-cell inhibitors include, without limitation, calcineurin inhibitors such as cyclosporine, tacrolimus and voclosporin, and mTOR inhibitors such as everolimus and sirolimus. Exemplary antimetabolites include, without limitation, purine antagonists such as azathioprine, dihydrofolate reductase (DHFR) inhibitors such as methotrexate, and inosine monophosphate dehydrogenase (IMPDH) inhibitors such as mycophenolate mofetil. Exemplary anti-TNF agents include, without limitation, adalimumab, certolizumab, golimumab, infliximab, and etanercept. Exemplary biologic agents include, without limitation, efalizumab, rituximab, abatacept, alemtuzumab, anakinra, canakinumab, gevokizumab, daclizumab, tocilizumab, secukinumab, interferon α/β, fingolimod, aflibercept, bevacizumab, ranibizumab, and intravenous immunoglobulin (IVIG). Exemplary alkylating agents include, without limitation, chlorambucil and cyclophosphamide. Exemplary cycloplegic agents include, without limitation, atropine and homatropine.

In certain embodiments, the method further comprises measuring levels of expression of CHIT1, MPO, LCN2, and LCP1 in the vitreous sample if the patient has a positive diagnosis for infectious uveitis, wherein increased levels of expression of CHIT1, MPO, LCN2, and LCP1 relative to reference value ranges for a control vitreous sample from an uninfected subject indicate that the patient has bacterial uveitis; and treating the patient for bacterial uveitis with an antibiotic, if the patient has a positive diagnosis for bacterial uveitis. Exemplary antibiotics include, without limitation, cephalosporins, vancomycin, ceftazidime, amikacin, gentamycin, and moxifloxacin.

In certain embodiments, the method further comprises measuring levels of expression of CST4, CNTN1, HPD, and MINP1 in the vitreous sample if the patient has a positive diagnosis for infectious uveitis, wherein increased levels of expression of CST4, CNTN1, HPD, and MINP1 relative to reference value ranges for a control vitreous sample from an uninfected subject indicate that the patient has viral uveitis; and treating the patient for viral uveitis with an antiviral agent, if the patient has a positive diagnosis for viral uveitis. Exemplary antiviral agents include, without limitation, ganciclovir, acyclovir, foscarnet, valacyclovir, and cidofivir.

In certain embodiments, the method further comprises measuring levels of expression of MMP8, CAP1, and SER-PINA3 in the vitreous sample, wherein increased levels of expression of MMP8, CAP1, and SERPINA3 relative to reference value ranges for a control vitreous sample from an uninfected subject indicate that the patient has fungal uveitis; and treating the patient for fungal uveitis with an antifungal agent, if the patient has a positive diagnosis for fungal uveitis. Exemplary antifungal agents include, without limitation, amphotericin B, voriconazole, caspofungin, and fluconazole.

In certain embodiments, the method further comprises performing a vitrectomy.

In certain embodiments, measuring the level of expression of a biomarker comprises measuring a level of expression of a protein. For example, levels of a biomarker protein may be measured by a method including, but not limited to, mass spectrometry or tandem mass spectrometry, an enzymatic or biochemical assay, liquid chromatography, NMR, or an immunoassay, such as an enzyme-linked immunosorbent assay (ELISA), a radioimmunoassay (RIA), an immunofluorescent assay (IFA), immunohistochemistry, fluorescence-activated cell sorting (FACS), or a Western Blot.

In another aspect, a method of monitoring bacterial uveitis in a patient is provided, the method comprising: a) obtaining a first vitreous sample from an eye of the patient at a first time point and a second vitreous sample from the eye of the subject later at a second time point; b) measuring levels of expression of one or more biomarkers in the first vitreous sample and the second vitreous sample, wherein the biomarkers are selected from the group consisting of CHIT1, MPO, LCN2, and LCP1; and c) analyzing the levels of expression of the one or more biomarkers in conjunction with respective reference value ranges for said biomarkers, wherein detection of increased levels of expression of the one or more biomarkers selected from the group consisting of CHIT1, MPO, LCN2, and LCP1 in the second vitreous sample compared to the first vitreous sample indicate that the patient is worsening, and detection of decreased levels of expression of the one or more biomarkers selected from the group consisting of CHIT1, MPO, LCN2, and LCP1 in the second vitreous sample compared to the first vitreous sample indicate that the patient is improving.

In another aspect, a method of monitoring efficacy of a treatment of a patient for bacterial uveitis is provided, the method comprising: a) obtaining a first vitreous sample from the patient before the patient undergoes the treatment and a second vitreous sample from the subject after the patient undergoes the treatment; b) measuring one or more biomarkers in the first vitreous sample and the second vitreous sample, wherein the biomarkers are selected from the group consisting of CHIT1, MPO, LCN2, and LCP1; and c) evaluating the efficacy of the treatment, wherein detection of increased levels of expression of CHIT1, MPO, LCN2, and LCP1 in the second vitreous sample compared to the first vitreous sample indicate that the patient is worsening or not responding to the treatment, and detection of decreased levels of expression of CHIT1, MPO, LCN2, and LCP1 in the second vitreous sample compared to the first vitreous sample indicate that the patient is improving. In certain embodiments, the method further comprises altering the treatment if the patient is worsening or not responding to the treatment.

In another aspect, a method of monitoring viral uveitis in a patient is provided, the method comprising: a) obtaining a first vitreous sample from an eye of the patient at a first time point and a second vitreous sample from the eye of the subject later at a second time point; b) measuring one or more biomarkers in the first vitreous sample and the second vitreous sample, wherein the biomarkers are selected from the group consisting of CST4, CNTN1, HPD, and MINP1; and c) analyzing the levels of expression of the one or more biomarkers in conjunction with respective reference value ranges for said biomarkers, wherein detection of increased levels of expression of the one or more biomarkers selected from the group consisting of CST4, CNTN1, HPD, and MINP1 in the second vitreous sample compared to the first vitreous sample indicate that the patient is worsening, and detection of decreased levels of expression of the one or more biomarkers selected from the group consisting of CST4, CNTN1, HPD, and MINP1 in the second vitreous sample compared to the first vitreous sample indicate that the patient is improving.

In another aspect, a method of monitoring efficacy of a treatment of a patient for viral uveitis is provided, the method comprising: a) obtaining a first vitreous sample from the patient before the patient undergoes the treatment and a second vitreous sample from the subject after the patient undergoes the treatment; b) measuring one or more biomarkers in the first vitreous sample and the second vitreous sample, wherein the biomarkers are selected from the group consisting of CST4, CNTN1, HPD, and MINP1; and c) evaluating the efficacy of the treatment, wherein detection of increased levels of expression of CST4, CNTN1, HPD, and MINP1 in the second vitreous sample compared to the first vitreous sample indicate that the patient is worsening or not responding to the treatment, and detection of decreased levels of expression of CST4, CNTN1, HPD, and MINP1 in the second vitreous sample compared to the first vitreous sample indicate that the patient is improving. In certain embodiments, the method further comprises altering the treatment if the patient is worsening or not responding to the treatment.

In another aspect, a method of monitoring fungal uveitis in a patient is provided, the method comprising: a) obtaining a first vitreous sample from an eye of the patient at a first time point and a second vitreous sample from the eye of the subject later at a second time point; b) measuring one or more biomarkers in the first vitreous sample and the second vitreous sample, wherein the biomarkers are selected from the group consisting of MMP8, CAP1, and SERPINA3; and c) analyzing the levels of expression of the one or more biomarkers in conjunction with respective reference value ranges for said biomarkers, wherein detection of increased levels of expression of the one or more biomarkers selected from the group consisting of MMP8, CAP1, and SERPINA3 in the second vitreous sample compared to the first vitreous sample indicate that the patient is worsening, and detection of decreased levels of expression of the one or more biomarkers selected from the group consisting of MMP8, CAP1, and SERPINA3 in the second vitreous sample compared to the first vitreous sample indicate that the patient is improving.

In another aspect, a method of monitoring efficacy of a treatment of a patient for fungal uveitis is provided, the method comprising: a) obtaining a first vitreous sample from the patient before the patient undergoes the treatment and a second vitreous sample from the subject after the patient undergoes the treatment; b) measuring one or more biomarkers in the first vitreous sample and the second vitreous sample, wherein the biomarkers are selected from the group consisting of MMP8, CAP1, and SERPINA3; and c) evaluating the efficacy of the treatment, wherein detection of increased levels of expression of MMP8, CAP1, and SERPINA3 in the second vitreous sample compared to the first vitreous sample indicate that the patient is worsening or not responding to the treatment, and detection of decreased levels of expression of MMP8, CAP1, and SERPINA3 in the second vitreous sample compared to the first vitreous sample indicate that the patient is improving. In certain embodiments, the method further comprises altering the treatment if the patient is worsening or not responding to the treatment.

In another aspect, a kit comprising agents for detecting at least 3 biomarkers selected from the group consisting of PGLYRP1, ELANE, MMP9, DEF1, S100A8, SPARCL1, LRP2, CNMD, CHIT1, MPO, LCN2, LCP1, CST4, CNTN1, HPD, MINP1, MMP8, CAP1, and SERPINA3 is provided. In some embodiments, the kit comprises agents for detecting a biomarker panel comprising or consisting of all of the PGLYRP1, ELANE, MMP9, DEF1, S100A8, SPARCL1, LRP2, CNMD, CHIT1, MPO, LCN2, LCP1, CST4, CNTN1, HPD, MINP1, MMP8, CAP1, and SERPINA3 biomarkers. In some embodiments, the kit comprises agents for detecting a biomarker panel comprising or consisting of the PGLYRP1, ELANE, MMP9, DEF1, S100A8, SPARCL1, LRP2, and CNMD biomarkers for distinguishing non-infectious uveitis from infectious uveitis. In some embodiments, the kit comprises agents for detecting a biomarker panel comprising or consisting of the CHIT1, MPO, LCN2, and LCP1 biomarkers for diagnosing bacterial uveitis. In some embodiments, the kit comprises agents for detecting a biomarker panel comprising or consisting of the CST4, CNTN1, HPD, and MINP1 biomarkers for diagnosing viral uveitis. In some embodiments, the kit comprises agents for detecting a biomarker panel comprising or consisting of the MMP8, CAP1, and SERPINA3 biomarkers for diagnosing fungal uveitis. In some embodiments, the kit further comprises instructions for determining whether a subject has non-infectious uveitis, bacterial uveitis, viral uveitis, or fungal uveitis.

In certain embodiments, the kit further comprises reagents for performing an immunoassay. In some embodiments, the kit comprises an antibody that specifically binds to peptidoglycan recognition protein 1 (PGLYRP1), an antibody that specifically binds to elastase, neutrophil expressed (ELANE), an antibody that specifically binds to matrix metalloproteinase-9 (MMP9), an antibody that specifically binds to DNA damage-responsive RNA polymerase-degradation factor (DEF1), an antibody that specifically binds to S100 calcium binding protein A8 (S100A8), an antibody that specifically binds to SPARC like 1 protein (SPARCL1), an antibody that specifically binds to LDL receptor related protein 2 (LRP2), an antibody that specifically binds to chondromodulin (CNMD), an antibody that specifically binds to chitotriosidase-1 (CHIT1), an antibody that specifically binds to myeloperoxidase (MPO), an antibody that specifically binds to lipocalin 2 (LCN2), an antibody that specifically binds to lymphocyte cytosolic protein 1 (LCP1), an antibody that specifically binds to cystatin S (CST4), an antibody that specifically binds to contactin-1 (CNTN1), an antibody that specifically binds to 4-hydroxyphenylpyruvate dioxygenase (HPD), an antibody that specifically binds to multiple inositol polyphosphate phosphatase 1 (MINP1), an antibody that specifically binds to matrix metallopeptidase 8

(MMP8), an antibody that specifically binds to cyclase associated actin cytoskeleton regulatory protein 1 (CAP1), and an antibody that specifically binds to serpin family A member 3 (SERPINA3).

In another aspect, a protein selected from the group consisting of peptidoglycan recognition protein 1 (PGLYRP1), elastase, neutrophil expressed (ELANE), matrix metalloproteinase-9 (MMP9), DNA damage-responsive RNA polymerase-degradation factor (DEF1), S100 calcium binding protein A8 (S100A8), SPARC like 1 protein (SPARCL1), LDL receptor related protein 2 (LRP2), chondromodulin (CNMD), chitotriosidase-1 (CHIT1), myeloperoxidase (MPO), lipocalin 2 (LCN2), lymphocyte cytosolic protein 1 (LCP1), cystatin S (CST4), contactin-1 (CNTN1), 4-hydroxyphenylpyruvate dioxygenase (HPD), multiple inositol polyphosphate phosphatase 1 (MINP1), matrix metallopeptidase 8 (MMP8), cyclase associated actin cytoskeleton regulatory protein 1 (CAP1), and serpin family A member 3 (SERPINA3) for use as a biomarker in diagnosing uveitis is provided.

In another aspect, an in vitro method of diagnosing uveitis is provided, the method comprising: a) obtaining a vitreous sample from an eye of the patient; b) measuring levels of expression of at least 3 biomarkers selected from the group consisting of PGLYRP1, ELANE, MMP9, DEF1, S100A8, SPARCL1, LRP2, and CNMD in the vitreous sample, wherein increased levels of expression of PGLYRP1, ELANE, MMP9, DEF1, S100A8 compared to reference value ranges for a vitreous sample from a subject having non-infectious uveitis indicate that the patient has infectious uveitis, and decreased levels of expression of SPARCL1, LRP2, and CNMD compared to reference value ranges for a vitreous sample from a subject having infectious uveitis indicate that the patient has non-infectious uveitis; c) measuring levels of expression of CHIT1, MPO, LCN2, and LCP1 in the vitreous sample if the patient has a positive diagnosis for infectious uveitis, wherein increased levels of expression of CHIT1, MPO, LCN2, and LCP1 relative to reference value ranges for a control vitreous sample from an uninfected subject indicate that the patient has bacterial uveitis; d) measuring levels of expression of CST4, CNTN1, HPD, and MINP1 in the vitreous sample if the patient has a positive diagnosis for infectious uveitis, wherein increased levels of expression of CST4, CNTN1, HPD, and MINP1 relative to reference value ranges for a control vitreous sample from an uninfected subject indicate that the patient has viral uveitis; and e) measuring levels of expression of MMP8, CAP1, and SERPINA3 in the vitreous sample, wherein increased levels of expression of MMP8, CAP1, and SERPINA3 relative to reference value ranges for a control vitreous sample from an uninfected subject indicate that the patient has fungal uveitis.

BRIEF DESCRIPTION OF THE DRAWINGS

FIG. 1A shows validation of proteomic biomarkers for infectious and non-infectious uveitis using multiplex ELISAs. FIG. 1B shows validation of specific biomarkers for different classes of infection.

FIGS. 2A-2D show a bio-repository for ophthalmic surgical specimens. FIG. 2A. Cross sectional image of the human eye. The vitreous is an extracellular matrix that covers the retina, lens, and ciliary body. The vitreous core is biopsied using a 23-gauge needle and contains native vitreous proteins, systemic, and retinal biomarkers. FIG. 2B.

After a liquid biopsy specimen has been collected in the operating room, it is centrifuged and then transferred to a micro centrifuge tube imprinted with a barcode. Next, the sample is scanned into the database using a scanner on the bench top. FIG. 2C. Two-dimensional barcode at the bottom of the tube. FIG. 2D. The sample is flash-frozen in liquid nitrogen and transported to the laboratory in a biohazard container.

(FIG. 3A) Principal component analysis (PCA) of the proteomics data. The score plot of PC1 and PC2 shows separation between non-infectious uveitis (blue), infectious (red), and controls (green; ERM). These results suggest that vitreous samples from infectious and non-infectious uveitis can be distinguished by their protein signatures. (FIG. 3B) Differentially-expressed proteins between infectious (red) and non-infectious uveitis (blue). Protein fold-changes represented as a volcano plot. The horizontal axis (x-axis) displays the log 2 fold-change value (infectious vs. non-infectious) and the vertical axis (y-axis) displays the noise-adjusted signal as the –log 10 (p-value) from the 1-way ANOVA analysis.

(FIG. 4A) Protein intensities were compared using 1-way ANOVA analysis and hierarchical heatmap clustering. Hierarchal clustering of proteins differentially expressed in our infectious endophthalmitis samples (all classes) compared to normal controls (ERM). Results are represented as a heatmap and display protein expression levels on a logarithmic scale. Orange indicates high expression while dark green/black indicates low or no expression. A total of 89 proteins were upregulated and a total of 88 proteins were downregulated (p<0.05). (FIG. 4B) Protein signatures were categorized by infection class (bacterial, viral, and fungal) and further analyzed by comparative Venn diagram analysis.

DETAILED DESCRIPTION OF THE INVENTION

Figure 1A:
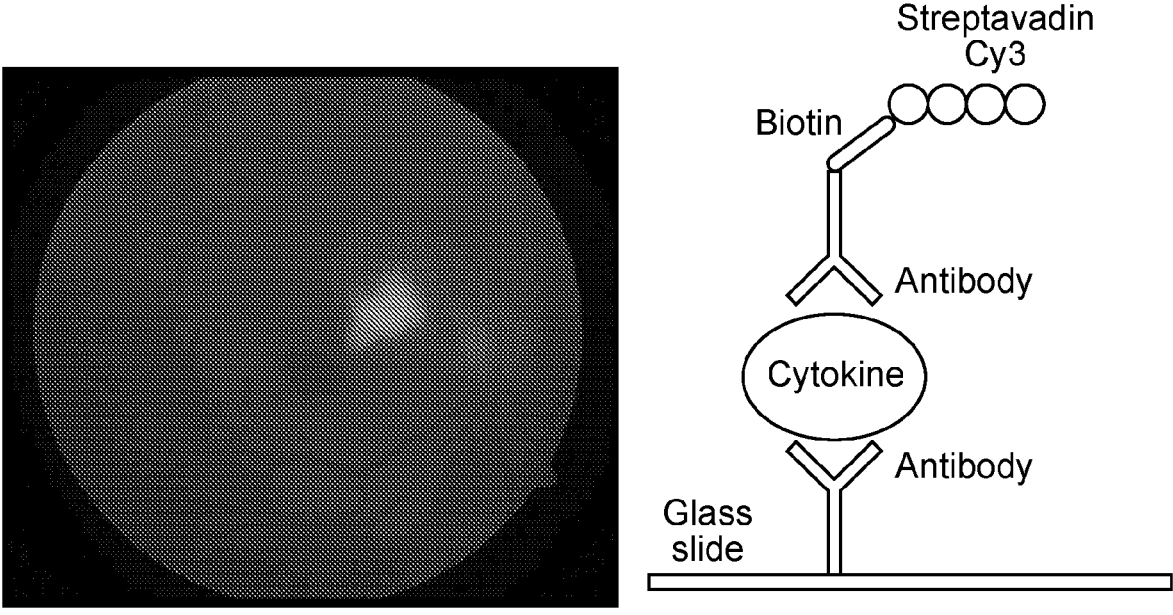
FIGS. 1A-1B show strategies for validating candidate proteomic markers for infectious endophthalmitis.
Figure 1B:
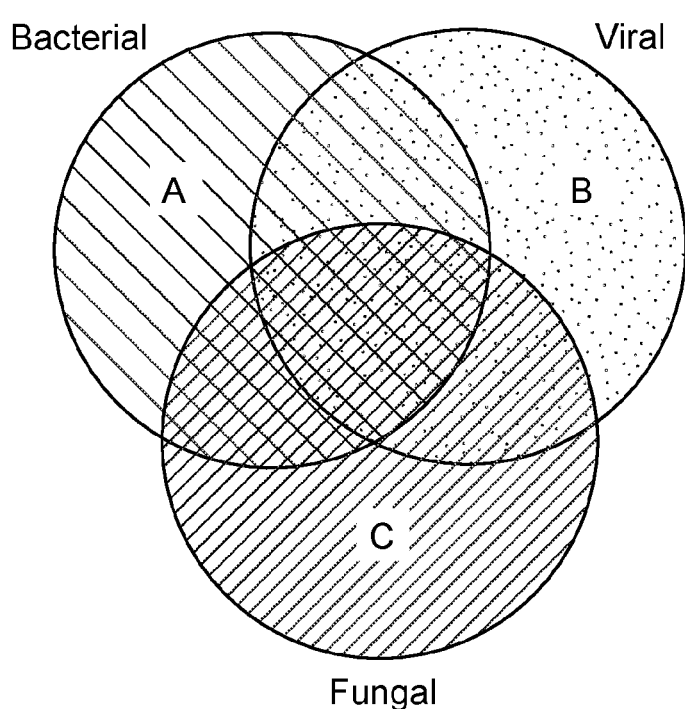

Compositions, methods, and kits are provided for diagnosing and treating uveitis. In particular, biomarkers have been identified that can be used to distinguish infectious uveitis from noninfectious uveitis, and further discriminate among bacterial, viral, and fungal uveitis. These biomarkers can be used alone or in combination with one or more additional biomarkers or relevant clinical parameters in prognosis, diagnosis, or monitoring treatment of uveitis.

Before the present compositions, methods, and kits are described, it is to be understood that this invention is not limited to particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a biomarker" includes a plurality of such biomarkers and reference to "the polypeptide" includes reference to one or more polypeptides and equivalents thereof, e.g. peptides or proteins known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Biomarkers. The term "biomarker" as used herein refers to a compound, such as a protein, a mRNA, a metabolite, or a metabolic byproduct which is differentially expressed or present at different concentrations, levels or frequencies in one sample compared to another, such as a vitreous sample from patients who have infectious or noninfectious uveitis compared to a vitreous sample from healthy control subjects (i.e., subjects not having uveitis or other inflammatory or infectious condition). Biomarkers include, but are not limited to, peptidoglycan recognition protein 1 (PGLYRP1), elastase, neutrophil expressed (ELANE), matrix metalloproteinase-9 (MMP9), DNA damage-responsive RNA polymerase-degradation factor (DEF1), S100 calcium binding protein A8 (S100A8), SPARC like 1 protein (SPARCL1), LDL receptor related protein 2 (LRP2), chondromodulin (CNMD), chitotriosidase-1 (CHIT1), myeloperoxidase (MPO), lipocalin 2 (LCN2), lymphocyte cytosolic protein 1 (LCP1), cystatin S (CST4), contactin-1 (CNTN1), 4-hydroxyphenylpyruvate dioxygenase (HPD), multiple inositol polyphosphate phosphatase 1 (MINP1), matrix metallopeptidase 8 (MMP8), cyclase associated actin cytoskeleton regulatory protein 1 (CAP1), and serpin family A member 3 (SERPINA3).

In some embodiments, the concentration or level of a biomarker is determined before and after the administration of a treatment to a patient. The treatment may comprise, for example, without limitation, administering an anti-inflammatory or immunosuppressive agent if the patient is diagnosed with non-infectious uveitis, an antibiotic if the patient is diagnosed with bacterial uveitis, an antiviral agent if the patient is diagnosed with viral uveitis, or an antifungal agent if the patient is diagnosed with fungal uveitis. The degree of change in the concentration or level of a biomarker, or lack thereof, is interpreted as an indication of whether the treatment has the desired effect (e.g., decreasing inflammation, preventing or reducing inflammatory damage, eradicating an infection). In other words, the concentration or level of a biomarker is determined before and after the administration of the treatment to an individual, and the degree of change, or lack thereof, in the level is interpreted as an indication of whether the individual is "responsive" to the treatment.

A "reference level" or "reference value" of a biomarker means a level of the biomarker that is indicative of a particular disease state, phenotype, or predisposition to developing a particular disease state or phenotype, or lack thereof, as well as combinations of disease states, phenotypes, or predisposition to developing a particular disease state or phenotype, or lack thereof. A "positive" reference level of a biomarker means a level that is indicative of a particular disease state or phenotype. A "negative" reference level of a biomarker means a level that is indicative of a lack of a particular disease state or phenotype. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched or gender-matched so that comparisons may be made between biomarker levels in samples from subjects of a certain age or gender and reference levels for a particular disease state, phenotype, or lack thereof in a certain age or gender group). Such reference levels may also be tailored to specific techniques that are used to measure levels of biomarkers in vitreous samples (e.g., immunoassays (e.g., ELISA), mass spectrometry (e.g., LC-MS, GC-MS), tandem mass spectrometry, NMR, biochemical or enzymatic assays, PCR, microarray analysis, etc.), where the levels of biomarkers may differ based on the specific technique that is used.

A "similarity value" is a number that represents the degree of similarity between two things being compared. For example, a similarity value may be a number that indicates the overall similarity between a patient's biomarker profile using specific phenotype-related biomarkers and reference value ranges for the biomarkers in one or more control samples or a reference profile (e.g., the similarity to a "non-infectious uveitis" biomarker expression profile, an "infectious uveitis" biomarker expression profile, a "bacterial uveitis" biomarker expression profile, a "viral uveitis" biomarker expression profile, or a "fungal uveitis" biomarker expression profile). The similarity value may be expressed as a similarity metric, such as a correlation coefficient, or may simply be expressed as the expression level difference, or the aggregate of the expression level differences, between levels of biomarkers in a patient sample and a control sample or reference expression profile.

The terms "quantity", "amount", and "level" are used interchangeably herein and may refer to an absolute quantification of a molecule or an analyte in a sample, or to a relative quantification of a molecule or analyte in a sample, i.e., relative to another value such as relative to a reference value as taught herein, or to a range of values for the biomarker. These values or ranges can be obtained from a single patient or from a group of patients.

Vitreous sample. The term "vitreous sample" with respect to an individual encompasses samples taken from the vitreous humor extracellular matrix located in the posterior chamber of the eye, such as a surgical or biopsy specimen isolated therefrom. Vitreous samples can be obtained by any suitable method such as by surgical resection or by biopsy, for example, using fine needle aspiration (FNA) or pars plana vitrectomy (PPV). The definition also includes samples that have been manipulated in any way after their procurement, such as by treatment with reagents; washed; or enriched for particular types of molecules, e.g., proteins, peptides, etc.

Obtaining and assaying a sample. The term "assaying" is used herein to include the physical steps of manipulating a vitreous sample to generate data related to the vitreous sample. As will be readily understood by one of ordinary skill in the art, a vitreous sample must be "obtained" prior to assaying the sample. Thus, the term "assaying" implies that the sample has been obtained. The terms "obtained" or "obtaining" as used herein encompass the act of receiving an extracted or isolated vitreous sample. For example, a testing facility can "obtain" a vitreous sample in the mail (or via delivery, etc.) prior to assaying the sample. In some such cases, the vitreous sample was "extracted" or "isolated" from an individual by another party prior to mailing (i.e., delivery, transfer, etc.), and then "obtained" by the testing facility upon arrival of the sample. Thus, a testing facility can obtain the sample and then assay the sample, thereby producing data related to the sample.

The terms "obtained" or "obtaining" as used herein can also include the physical extraction or isolation of a vitreous sample from a subject. Accordingly, a vitreous sample can be isolated from a subject (and thus "obtained") by the same person or same entity that subsequently assays the sample. When a vitreous sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a vitreous sample.

In some embodiments, the step of obtaining comprises the step of isolating a vitreous sample (e.g., a pre-treatment vitreous sample, a post-treatment vitreous sample, etc.). Methods and protocols for isolating various vitreous samples (e.g., a blood sample, a serum sample, a plasma sample, a biopsy sample, an aspirate, etc.) will be known to one of ordinary skill in the art and any convenient method may be used to isolate a vitreous sample.

It will be understood by one of ordinary skill in the art that in some cases, it is convenient to wait until multiple samples (e.g., a pre-treatment vitreous sample and a post-treatment vitreous sample) have been obtained prior to assaying the samples. Accordingly, in some cases an isolated vitreous sample (e.g., a pre-treatment vitreous sample, a post-treatment vitreous sample, etc.) is stored until all appropriate samples have been obtained. One of ordinary skill in the art will understand how to appropriately store a variety of different types of vitreous samples and any convenient method of storage may be used (e.g., refrigeration) that is appropriate for the particular vitreous sample. In some embodiments, a pre-treatment vitreous sample is assayed prior to obtaining a post-treatment vitreous sample. In some cases, a pre-treatment vitreous sample and a post-treatment vitreous sample are assayed in parallel. In some cases, multiple different post-treatment vitreous samples and/or a pre-treatment vitreous sample are assayed in parallel. In some cases, vitreous samples are processed immediately or as soon as possible after they are obtained.

In some embodiments, the concentration (i.e., "level"), or expression level of a gene product, which may be a protein, peptide, etc., (which will be referenced herein as a bio-marker), in a vitreous sample is measured (i.e., "deter-mined"). By "expression level" (or "level") it is meant the level of gene product (e.g. the absolute and/or normalized value determined for the RNA expression level of a bio-marker or for the expression level of the encoded polypep-tide, or the concentration of the protein in a vitreous sample). The term "gene product" or "expression product" are used herein to refer to the RNA transcription products (RNA transcripts, e.g. mRNA, an unspliced RNA, a splice variant mRNA, and/or a fragmented RNA) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant poly-peptide, etc.

The terms "determining", "measuring", "evaluating", "assessing," "assaying," and "analyzing" are used inter-changeably herein to refer to any form of measurement, and include determining if an element is present or not. These terms include both quantitative and/or qualitative determi-nations. Assaying may be relative or absolute. For example, "assaying" can be determining whether the expression level is less than or "greater than or equal to" a particular threshold, (the threshold can be pre-determined or can be determined by assaying a control sample). On the other hand, "assaying to determine the expression level" can mean determining a quantitative value (using any convenient metric) that represents the level of expression (i.e., expres-sion level, e.g., the amount of protein and/or RNA, e.g., mRNA) of a particular biomarker. The level of expression can be expressed in arbitrary units associated with a par-ticular assay (e.g., fluorescence units, e.g., mean fluores-cence intensity (MFI)), or can be expressed as an absolute value with defined units (e.g., number of mRNA transcripts, number of protein molecules, concentration of protein, etc.). Additionally, the level of expression of a biomarker can be compared to the expression level of one or more additional genes (e.g., nucleic acids and/or their encoded proteins) to derive a normalized value that represents a normalized expression level. The specific metric (or units) chosen is not crucial as long as the same units are used (or conversion to the same units is performed) when evaluating multiple vitreous samples from the same individual (e.g., vitreous samples taken at different points in time from the same individual). This is because the units cancel when calculat-ing a fold-change (i.e., determining a ratio) in the expression level from one vitreous sample to the next (e.g., vitreous samples taken at different points in time from the same individual).

For measuring RNA levels, the amount or level of an RNA in the sample is determined, e.g., the level of an mRNA. In some instances, the expression level of one or more additional RNAs may also be measured, and the level of biomarker expression compared to the level of the one or more additional RNAs to provide a normalized value for the biomarker expression level. Any convenient protocol for evaluating RNA levels may be employed wherein the level of one or more RNAs in the assayed sample is determined.

For measuring protein levels, the amount or level of a protein in the vitreous sample is determined. In some cases, the protein comprises a post-translational modification (e.g., phosphorylation, glycosylation) associated with regulation of activity of the protein such as by a signaling cascade, wherein the modified protein is the biomarker, and the amount of the modified protein is therefore measured. In some embodiments, an extracellular protein level is mea-sured. For example, in some cases, the protein (i.e., poly-peptide) being measured is a secreted protein (e.g., extra-cellular matrix protein) and the concentration can therefore be measured in vitreous fluid. In some embodiments, con-centration is a relative value measured by comparing the level of one protein relative to another protein. In other embodiments the concentration is an absolute measurement of weight/volume or weight/weight.

In some instances, the concentration of one or more additional proteins may also be measured, and biomarker concentration compared to the level of the one or more additional proteins to provide a normalized value for the biomarker concentration. Any convenient protocol for evaluating protein levels may be employed wherein the level of one or more proteins in the assayed sample is determined.

While a variety of different manners of assaying for protein levels are known to one of ordinary skill in the art and any convenient method may be used, one representative and convenient type of protocol for assaying protein levels is ELISA, an antibody-based method. In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is con-tacted with the sample to be tested under conditions that are conducive to immune complex (antigen/antibody) forma-tion. Following incubation, the antisera-contacted surface is washed so as to remove non-immunocomplexed material. The occurrence and amount of immunocomplex formation may then be determined by subjecting the bound immuno-complexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. After such incubation with the second antibody and washing to remove unbound material, the amount of label is quantified, for example by incubation with a chromogenic substrate such as urea and bromocresol purple in the case of a urease label or 2,2'-azino-di-(3-ethyl-benzthiazoline)-6-sulfonic acid (ABTS) and $H_2O_2$, in the case of a peroxidase label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody. The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be effected in a manner most appropriate for the substrate being used, for example, by removing a bead or dipstick from a reservoir, emptying or diluting a reservoir such as a microtiter plate well, or rinsing a bead, particle, chromatographic column or filter with a wash solution or solvent.

Alternatively, non-ELISA based-methods for measuring the levels of one or more proteins in a sample may be employed. Representative exemplary methods include but are not limited to antibody-based methods (e.g., immuno-fluorescence assay, radioimmunoassay, immunoprecipitation, Western blotting, proteomic arrays, xMAP microsphere technology (e.g., Luminex technology), immunohistochemistry, flow cytometry, and the like) as well as non-antibody-based methods (e.g., mass spectrometry or tandem mass spectrometry).

"Diagnosis" as used herein generally includes determination as to whether a subject is likely affected by a given disease, disorder or dysfunction. The skilled artisan often makes a diagnosis on the basis of one or more diagnostic indicators, i.e., a biomarker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

Additional Terms.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) prevent-ing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with uveitis, those with ocular inflammation or infection, etc.) as well as those in which prevention is desired (e.g., those with increased susceptibility to uveitis, those with an increased likelihood of ocular infection, those suspected of having uveitis, those suspected of harboring an ocular infection, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

The term "about," particularly in reference to a given quantity, is meant to encompass deviations of plus or minus five percent.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

A "therapeutically effective dose" or "therapeutic dose" is an amount sufficient to effect desired clinical results (i.e., achieve therapeutic efficacy). A therapeutically effective dose can be administered in one or more administrations.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer. Both full-length proteins and fragments thereof are encompassed by the definition. The terms also include postexpression modifications of the polypeptide, for example, phosphorylation, glycosylation, acetylation, hydroxylation, oxidation, and the like.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), and any other type of polynucleotide which is an N- or C-glycoside of a purine or pyrimidine base. There is no intended distinction in length between the terms "polynucleotide," "oligonucleotide," "nucleic acid" and "nucleic acid molecule," and these terms are used interchangeably.

By "isolated" is meant, when referring to a protein, polypeptide, or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "antibody" encompasses monoclonal antibodies, polyclonal antibodies, as well as hybrid antibodies, altered antibodies, chimeric antibodies, and humanized antibodies. The term antibody includes: hybrid (chimeric) antibody molecules (see, for example, Winter et al. (1991) *Nature* 349:293-299; and U.S. Pat. No. 4,816,567); bispecific antibodies, bispecific T cell engager antibodies (BITE), trispecific antibodies, and other multispecific antibodies (see, e.g., Fan et al. (2015) *J. Hematol. Oncol.* 8:130, Krishnamurthy et al. (2018) *Pharmacol Ther.* 185:122-134), $F(ab')_2$ and F(ab) fragments; $F_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (scFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911: 15-26; dimeric and trimeric antibody fragment constructs; minibodies (see, e.g., Pack et al. (1992) *Biochem* 31:1579-1584; Cumber et al. (1992) *J Immunology* 1496:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276, 169, published 21 Sep. 1994); and, any functional fragments obtained from such molecules, wherein such fragments retain specific-binding properties of the parent antibody molecule.

The phrase "specifically (or selectively) binds" with reference to binding of an antibody to an antigen (e.g., biomarker) refers to a binding reaction that is determinative of the presence of the antigen in a heterogeneous population of proteins and other biologics. Thus, under designated immunoassay conditions, the specified antibodies bind to a particular antigen at least two times over the background and do not substantially bind in a significant amount to other antigens present in the sample. Specific binding to an antigen under such conditions may require an antibody that is selected for its specificity for a particular antigen. For example, antibodies raised to an antigen from specific species such as rat, mouse, or human can be selected to obtain only those antibodies that are specifically immunoreactive with the antigen and not with other proteins, except for polymorphic variants and alleles. This selection may be achieved by subtracting out antibodies that cross-react with molecules from other species. A variety of immunoassay formats may be used to select antibodies specifically immunoreactive with a particular antigen. For example, solid-phase ELISA immunoassays are routinely used to select antibodies specifically immunoreactive with a protein (see, e.g., Harlow & Lane. Antibodies, A Laboratory Manual (1988), for a description of immunoassay formats and conditions that can be used to determine specific immunoreactivity). Typically, a specific or selective reaction will be at least twice background signal or noise and more typically more than 10 to 100 times background.

"Providing an analysis" is used herein to refer to the delivery of an oral or written analysis (i.e., a document, a report, etc.). A written analysis can be a printed or electronic document. A suitable analysis (e.g., an oral or written report) provides any or all of the following information: identifying information of the subject (name, age, etc.), a description of what type of vitreous sample(s) was used and/or how it was used, the technique used to assay the sample, the results of the assay (e.g., the level of the biomarker as measured and/or the fold-change of a biomarker level over time or in a post-treatment assay compared to a pre-treatment assay), the assessment as to whether the individual is determined to have infectious or non-infectious uveitis, a recommendation for treatment (e.g., anti-inflammatory or immunosuppressive agent for non-infectious uveitis, or an antibiotic, anti-viral agent, or antifungal agent for infectious uveitis), and/or to continue or alter therapy, a recommended strategy for additional therapy, etc. The report can be in any format including, but not limited to printed information on a suitable medium or substrate (e.g., paper); or electronic format. If in electronic format, the report can be in any computer readable medium, e.g., diskette, compact disk (CD), flash drive, and the like, on which the information has been recorded. In addition, the report may be present as a website address which may be used via the internet to access the information at a remote site.

Biomarkers and Diagnostic Methods

Biomarkers that can be used in the practice of the subject methods include, without limitation, peptidoglycan recognition protein 1 (PGLYRP1), elastase, neutrophil expressed (ELANE), matrix metalloproteinase-9 (MMP9), DNA damage-responsive RNA polymerase-degradation factor (DEF1), S100 calcium binding protein A8 (S100A8), SPARC like 1 protein (SPARCL1), LDL receptor related protein 2 (LRP2), chondromodulin (CNMD), chitotriosidase-1 (CHIT1), myeloperoxidase (MPO), lipocalin 2 (LCN2), lymphocyte cytosolic protein 1 (LCP1), cystatin S (CST4), contactin-1 (CNTN1), 4-hydroxyphenylpyruvate dioxygenase (HPD), multiple inositol polyphosphate phosphatase 1 (MINP1), matrix metallopeptidase 8 (MMP8), cyclase associated actin cytoskeleton regulatory protein 1 (CAP1), and serpin family A member 3 (SERPINA3). Differential expression of these biomarkers is associated with uveitis and therefore expression profiles of these biomarkers are useful for diagnosing uveitis. Biomarker expression profiles can be used to distinguish infectious uveitis from non-infectious uveitis and further determine if a patient with infectious uveitis has bacterial, viral, or fungal uveitis.

In certain embodiments, a panel of biomarkers is used for diagnosis of uveitis. Biomarker panels of any size can be used in the practice of the subject methods. Biomarker panels for diagnosing uveitis typically comprise at least 3 biomarkers and up to 20 biomarkers, including any number of biomarkers in between, such as 3, 4, 5, 6, 7, 8, 9, 10, 11, 12, 13, 14, 15, 16, 17, 18, 19, or 20 biomarkers. In certain embodiments, a biomarker panel comprising at least 3, or at least 4, or at least 5, or at least 6, or at least 7, or at least 8, or at least 9, or at least 10, or at least 11, or at least 12, or at least 13, or at least 14, or at least 5, or at least 16, or at least 17, or at least 18, or at least 19, or more biomarkers. In some embodiments, the biomarker panel comprises or consists of all of the PGLYRP1, ELANE, MMP9, DEF1, S100A8, SPARCL1, LRP2, CNMD, CHIT1, MPO, LCN2, LCP1, CST4, CNTN1, HPD, MINP1, MMP8, CAP1, and SERPINA3 biomarkers. In some embodiments, the biomarker panel comprises or consists of the PGLYRP1, ELANE, MMP9, DEF1, S100A8, SPARCL1, LRP2, and CNMD biomarkers for distinguishing non-infectious uveitis from infectious uveitis. In some embodiments, the biomarker panel comprises or consists of the CHIT1, MPO, LCN2, and LCP1 biomarkers for diagnosing bacterial uveitis. In some embodiments, the biomarker panel comprises or consists of the CST4, CNTN1, HPD, and MINP1 biomarkers for diagnosing viral uveitis. In some embodiments, the biomarker panel comprises or consists of the MMP8, CAP1, and SERPINA3 biomarkers for diagnosing fungal uveitis. Although smaller biomarker panels are usually more economical, larger biomarker panels (i.e., greater than 20 biomarkers) have the advantage of providing more detailed information and can also be used in the practice of the subject methods.

A vitreous sample comprising the expressed biomarkers is obtained from the subject. The sample is taken from the vitreous humor extracellular matrix located in the posterior chamber of the eye of the subject. A "control" sample, as used herein, refers to a vitreous sample from a subject that is not diseased. That is, a control sample is obtained from a normal or healthy subject (e.g. an individual known to not have uveitis or ocular inflammation or an infection). A vitreous sample can be obtained from a subject by conventional techniques. For example, vitreous samples can be obtained by surgical resection or by biopsy using fine needle aspiration (FNA) or pars plana vitrectomy (PPV) according to methods well known in the art.

When analyzing the levels of biomarkers in a vitreous sample from a subject, the reference value ranges used for comparison can represent the levels of one or more biomarkers in a vitreous sample from one or more subjects without uveitis (i.e., normal or healthy control). Alternatively, the reference values can represent the levels of one or more biomarkers from one or more subjects with uveitis, wherein similarity to the reference value ranges indicates the subject has uveitis. More specifically, the reference value ranges can represent the levels of one or more biomarkers from one or more subjects with non-infectious uveitis (a "non-infectious uveitis biomarker expression profile") or infectious uveitis (an "infectious uveitis biomarker expression profile") to determine if the patient has non-infectious or infectious uveitis. If a patient is diagnosed with infectious uveitis based on similarity to an "infectious uveitis" biomarker expression profile, further comparison to reference value ranges for the levels of the biomarkers in subjects with bacterial uveitis (e.g., a "bacterial uveitis biomarker expression profile"), viral uveitis (a "viral uveitis biomarker expression profile"), or fungal uveitis (a "fungal uveitis biomarker expression profile") can be used to determine if the patient has bacterial, viral, or fungal uveitis, respectively.

Accordingly, in one aspect, a method is provided for determining if a patient has non-infectious uveitis or infectious uveitis. The method comprises obtaining a vitreous sample from an eye of the patient; and measuring levels of expression of one or more biomarkers selected from the group consisting of PGLYRP1, ELANE, MMP9, DEF1, S100A8, SPARCL1, LRP2, and CNMD in the vitreous sample, wherein increased levels of expression of PGLYRP1, ELANE, MMP9, DEF1, S100A8 compared to reference value ranges for a vitreous sample from a subject having non-infectious uveitis indicate that the patient has infectious uveitis, and decreased levels of expression of SPARCL1, LRP2, and CNMD compared to reference value ranges for a vitreous sample from a subject having infectious uveitis indicate that the patient has non-infectious uveitis.

If a patient is determined to have infectious uveitis, biomarker expression profiles can be further used in diagnosing the patient to distinguish among bacterial, viral, or fungal uveitis as follows: In order to determine if the patient has bacterial uveitis, the levels of expression of CHIT1, MPO, LCN2, and LCP1 are measured in the vitreous sample, wherein increased levels of expression of CHIT1, MPO, LCN2, and LCP1 relative to reference value ranges for a control vitreous sample from an uninfected subject indicate that the patient has bacterial uveitis. In order to determine if the patient has viral uveitis the levels of expression of CST4, CNTN1, HPD, and MINP1 are measured in the vitreous sample, wherein increased levels of expression of CST4, CNTN1, HPD, and MINP1 relative to reference value ranges for a control vitreous sample from an uninfected subject indicate that the patient has viral uveitis. In order to determine if the patient has fungal uveitis the levels of expression of MMP8, CAP1, and SERPINA3 are measured in the vitreous sample, wherein increased levels of expression of MMP8, CAP1, and SERPINA3 relative to reference value ranges for a control vitreous sample from an uninfected subject indicate that the patient has fungal uveitis;

The methods described herein may be used to determine an appropriate treatment regimen for a patient and, in particular, whether a patient should be treated for infectious or non-infectious uveitis. For example, a patient is selected for treatment for non-infectious uveitis if the patient has a positive diagnosis for non-infectious uveitis based on a biomarker expression profile, as described herein. The treatment for non-infectious uveitis may comprise, for example, administering a therapeutically effective amount of one or more anti-inflammatory or immunosuppressive agents such as, but not limited to, glucocorticoid steroids including, without limitation, prednisolone, methylprednisolone, iluvien, ozurdex, retisert, and triamcinolone; T-cell inhibitors including, without limitation, calcineurin inhibitors such as cyclosporine, tacrolimus and voclosporin, and mTOR inhibitors such as everolimus and sirolimus; antimetabolites including, without limitation, purine antagonists such as azathioprine, dihydrofolate reductase (DHFR) inhibitors such as methotrexate, and inosine monophosphate dehydrogenase (IMPDH) inhibitors such as mycophenolate mofetil; anti-TNF agents including, without limitation, adalimumab, certolizumab, golimumab, infliximab, and etanercept; biologic agents including, without limitation, efalizumab, rituximab, abatacept, alemtuzumab, anakinra, canakinumab, gevokizumab, daclizumab, tocilizumab, secukinumab, interferon α/β, fingolimod, aflibercept, bevacizumab, ranibizumab, and intravenous immunoglobulin (IVIG); alkylating agents including, without limitation, chlorambucil and cyclophosphamide; and cycloplegic agents including, without limitation, atropine and homatropine; or a combination thereof.

A patient is selected for treatment for bacterial uveitis if the patient has a positive diagnosis for infectious uveitis and is further determined to have bacterial uveitis based on a biomarker expression profile. The treatment for bacterial uveitis may comprise, for example, administering a therapeutically effective amount of one or more antibiotics such as, but not limited to, vancomycin, ceftazidime, amikacin, gentamycin, moxifloxacin, and cephalosporins such as cefacetrile (cephacetrile), cefadroxil (cefadroxyl; Duricef), cefalexin (cephalexin; Keflex), cefaloglycin (cephaloglycin), cefalonium (cephalonium), cefaloridine (cephaloradine), cefalotin (cephalothin; Keflin), cefapirin (cephapirin; Cefadryl), cefatrizine, cefazaflur, cefazedone, cefazolin (cephazolin; Ancef, Kefzol), cefradine (cephradine; Velosef), cefroxadine, ceftezole, cefaclor (Ceclor, Distaclor, Keflor, Raniclor), cefonicid (Monocid), cefprozil (cefproxil; Cefzil), cefuroxime (Zefu, Zinnat, Zinacef, Ceftin, Biofuroksym, Xorimax), cefuzonam, cefmetazole, cefotetan, cefoxitin, loracarbef (Lorabid), cefbuperazone, cefmetazole (Zefazone), cefminox, cefotetan (Cefotan), cefoxitin (Mefoxin), cefotiam (Pansporin), cefcapene, cefdaloxime, cefdinir (Sefdin, Zinir, Omnicef, Kefnir), cefditoren, cefetamet, cefixime (Fixx, Zifi, Suprax), cefmenoxime, cefodizime, cefotaxime (Claforan), cefovecin (Convenia), cefpimizole, cefpodoxime (Vantin, PECEF, Simplicef), cefteram, ceftibuten (Cedax), ceftiofur (Naxcel, Excenel), ceftiolene, ceftizoxime (Cefizox), ceftriaxone (Rocephin), cefoperazone (Cefobid), ceftazidime (Meezat, Fortum, Fortaz), latamoxef (moxalactam), cefclidine, cefepime (Maxipime), cefluprenam, cefoselis, cefozopran, cefpirome (Cefrom), cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; or a combination thereof.

A patient is selected for treatment for viral uveitis if the patient has a positive diagnosis for infectious uveitis and is further determined to have viral uveitis based on a biomarker expression profile. The treatment for viral uveitis may comprise, for example, administering a therapeutically effective amount of one or more antiviral agents such as, but not limited to, ganciclovir, acyclovir, foscarnet, valacyclovir, and cidofivir, or a combination thereof.

A patient is selected for treatment for fungal uveitis if the patient has a positive diagnosis for infectious uveitis and is further determined to have fungal uveitis based on a biomarker expression profile. The treatment for fungal uveitis may comprise, for example, administering a therapeutically effective amount of one or more antifungal agents such as, but not limited to, amphotericin B, voriconazole, caspofungin, and fluconazole, or a combination thereof.

In some embodiments, the methods described herein are used for monitoring uveitis in a subject. For example, a first vitreous sample can be obtained from the patient at a first time point and a second vitreous sample can be obtained from the subject at a second (later) time point. In one embodiment, bacterial uveitis is monitored in the patient by measuring levels of expression of one or more biomarkers selected from the group consisting of CHIT1, MPO, LCN2, and LCP1 in the first vitreous sample and the second vitreous sample; and analyzing the levels of expression of the one or more biomarkers in conjunction with respective reference value ranges for the biomarkers, wherein detection of increased levels of expression of one or more biomarkers selected from the group consisting of CHIT1, MPO, LCN2, and LCP1 in the second vitreous sample compared to the first vitreous sample indicate that the patient is worsening, and detection of decreased levels of expression of one or more biomarkers selected from the group consisting of CHIT1, MPO, LCN2, and LCP1 in the second vitreous sample compared to the first vitreous sample indicate that the patient is improving.

In another embodiment, viral uveitis is monitored in the patient by measuring levels of expression of one or more biomarkers selected from the group consisting of CST4, CNTN1, HPD, and MINP1 in the first vitreous sample and the second vitreous sample; and analyzing the levels of expression of the one or more biomarkers in conjunction with respective reference value ranges for the biomarkers, wherein detection of increased levels of expression of one or more biomarkers selected from the group consisting of CST4, CNTN1, HPD, and MINP1 in the second vitreous sample compared to the first vitreous sample indicate that the patient is worsening, and detection of decreased levels of expression of one or more biomarkers selected from the group consisting of CST4, CNTN1, HPD, and MINP1 in the second vitreous sample compared to the first vitreous sample indicate that the patient is improving.

In another embodiment, fungal uveitis is monitored in the patient by measuring levels of expression of one or more biomarkers selected from the group consisting of MMP8, CAP1, and SERPINA3 in the first vitreous sample and the second vitreous sample; and analyzing the levels of expression of the one or more biomarkers in conjunction with respective reference value ranges for the biomarkers, wherein detection of increased levels of expression of one or more biomarkers selected from the group consisting of MMP8, CAP1, and SERPINA3 in the second vitreous sample compared to the first vitreous sample indicate that the patient is worsening, and detection of decreased levels of expression of one or more biomarkers selected from the group consisting of MMP8, CAP1, and SERPINA3 in the second vitreous sample compared to the first vitreous sample indicate that the patient is improving.

The subject methods may also be used for assaying pre-treatment and post-treatment vitreous samples obtained from an individual to determine whether the individual is responsive or not responsive to a treatment. For example, a first vitreous sample can be obtained from a subject before the subject undergoes the therapy, and a second vitreous sample can be obtained from the subject after the subject undergoes the therapy. In one embodiment, the efficacy of a treatment of a patient for bacterial uveitis is monitored by measuring one or more biomarkers selected from the group consisting of CHIT1, MPO, LCN2, and LCP1 in the first vitreous sample and the second vitreous sample; and evaluating the efficacy of the treatment, wherein detection of increased levels of expression of CHIT1, MPO, LCN2, and LCP1 in the second vitreous sample compared to the first vitreous sample indicate that the patient is worsening or not responding to the treatment, and detection of decreased levels of expression of CHIT1, MPO, LCN2, and LCP1 in the second vitreous sample compared to the first vitreous sample indicate that the patient is improving.

In another embodiment, the efficacy of a treatment of a patient for viral uveitis is monitored by measuring one or more biomarkers selected from the group consisting of CST4, CNTN1, HPD, and MINP1 in the first vitreous sample and the second vitreous sample; and evaluating the efficacy of the treatment, wherein detection of increased levels of expression of CST4, CNTN1, HPD, and MINP1 in the second vitreous sample compared to the first vitreous sample indicate that the patient is worsening or not responding to the treatment, and detection of decreased levels of expression of CST4, CNTN1, HPD, and MINP1 in the second vitreous sample compared to the first vitreous sample indicate that the patient is improving.

In another embodiment, the efficacy of a treatment of a patient for fungal uveitis is monitored by measuring one or more biomarkers selected from the group consisting of MMP8, CAP1, and SERPINA3 in the first vitreous sample and the second vitreous sample; and evaluating the efficacy of the treatment, wherein detection of increased levels of expression of MMP8, CAP1, and SERPINA3 in the second vitreous sample compared to the first vitreous sample indicate that the patient is worsening or not responding to the treatment, and detection of decreased levels of expression of MMP8, CAP1, and SERPINA3 in the second vitreous sample compared to the first vitreous sample indicate that the patient is improving.

In some cases, combinations of biomarkers are used in the subject methods. In some such cases, the levels of all measured biomarkers must change (as described above) in order for the diagnosis to be made. In some embodiments, only some biomarkers are used in the methods described herein. For example, a single biomarker, 2 biomarkers, 3 biomarkers, 4 biomarkers, 5 biomarkers, 6 biomarkers, 7 biomarkers, 8 biomarkers, 9 biomarkers, 10 biomarkers, 11 biomarkers, 12 biomarkers, 13 biomarkers, 14 biomarkers, 15 biomarkers, 16 biomarkers, 17 biomarkers, 18 biomarkers, or 19 biomarkers can be used in any combination. In other embodiments, all the biomarkers are used. The quantitative values may be combined in linear or non-linear fashion to calculate one or more risk scores for uveitis for the individual, including further classifying uveitis as non-infectious or infectious uveitis, and in the case of infectious uveitis, more specifically by type of infectious uveitis (i.e., bacterial, viral, or fungal uveitis).

The level of a biomarker in a pre-treatment vitreous sample can be referred to as a "pre-treatment value" because the first vitreous sample is isolated from the individual prior to the administration of the therapy (i.e., "pre-treatment"). The level of a biomarker in the pre-treatment vitreous sample can also be referred to as a "baseline value" because this value is the value to which "post-treatment" values are compared. In some cases, the baseline value (i.e., "pre-treatment value") is determined by determining the level of a biomarker in multiple (i.e., more than one, e.g., two or more, three or more, for or more, five or more, etc.) pre-treatment vitreous samples. In some cases, the multiple pre-treatment vitreous samples are isolated from an individual at different time points in order to assess natural fluctuations in biomarker levels prior to treatment. As such, in some cases, one or more (e.g., two or more, three or more, for or more, five or more, etc.) pre-treatment vitreous samples are isolated from the individual. In some embodiments, all of the pre-treatment vitreous samples will be the same type of vitreous sample (e.g., a biopsy sample). In some cases, two or more pre-treatment vitreous samples are pooled prior to determining the level of the biomarker in the vitreous samples. In some cases, the level of the biomarker is determined separately for two or more pre-treatment vitreous samples and a "pre-treatment value" is calculated by averaging the separate measurements.

A post-treatment vitreous sample is isolated from an individual after the administration of a therapy. Thus, the level of a biomarker in a post-treatment sample can be referred to as a "post-treatment value". In some embodiments, the level of a biomarker is measured in additional post-treatment vitreous samples (e.g., a second, third, fourth, fifth, etc. post-treatment vitreous sample). Because additional post-treatment vitreous samples are isolated from the individual after the administration of a treatment, the levels of a biomarker in the additional vitreous samples can also be referred to as "post-treatment values."

The term "responsive" as used herein means that the treatment is having the desired effect such as reducing ocular inflammation, preventing or decreasing inflammatory damage, and/or eradicating an ocular infection. When the individual does not improve in response to the treatment, it may be desirable to seek a different therapy or treatment regime for the individual.

The determination that an individual has non-infectious uveitis or infectious uveitis is an active clinical application of the correlation between levels of a biomarker and the disease. For example, "determining" requires the active step of reviewing the data, which is produced during the active assaying step(s), and resolving whether an individual does or does not have non-infectious uveitis or infectious uveitis or is responding or not responding to a therapy for treatment of non-infectious or infectious uveitis. Additionally, in some cases, a decision is made to proceed with the current treatment (i.e., therapy), or instead to alter the treatment. In some cases, the subject methods include the step of continuing therapy or altering therapy.

The term "continue treatment" (i.e., continue therapy) is used herein to mean that the current course of treatment (e.g., continued administration of a therapy) is to continue. If the current course of treatment is not effective in treating non-infectious or infectious uveitis, the treatment may be altered. "Altering therapy" is used herein to mean "discontinuing therapy" or "changing the therapy" (e.g., changing the type of treatment, changing the particular dose and/or frequency of administration of medication, e.g., increasing the dose and/or frequency). In some cases, therapy can be altered until the individual is deemed to be responsive. In some embodiments, altering therapy means changing which type of treatment is administered, discontinuing a particular treatment altogether, etc.

As a non-limiting illustrative example, a patient may be initially treated by putting the patient on an antibiotic for treating bacterial uveitis. Then to "continue treatment" would be to continue with this type of treatment. If the current course of treatment is not effective in eradicating the infection (e.g., bacteria resistant to the antibiotic), the treatment may be altered, e.g., switching treatment to a different antibiotic or adding additional antibiotics to the treatment.

In other words, the level of one or more biomarkers may be monitored in order to determine when to continue therapy and/or when to alter therapy. As such, a post-treatment vitreous sample can be isolated after any of the administrations and the vitreous sample can be assayed to determine the level of a biomarker. Accordingly, the subject methods can be used to determine whether an individual being treated for uveitis is responsive or is maintaining responsiveness to a treatment.

The therapy can be administered to an individual any time after a pre-treatment vitreous sample is isolated from the individual, but it is preferable for the therapy to be administered simultaneous with or as soon as possible (e.g., about 7 days or less, about 3 days or less, e.g., 2 days or less, 36 hours or less, 1 day or less, 20 hours or less, 18 hours or less, 12 hours or less, 9 hours or less, 6 hours or less, 3 hours or less, 2.5 hours or less, 2 hours or less, 1.5 hours or less, 1 hour or less, 45 minutes or less, 30 minutes or less, 20 minutes or less, 15 minutes or less, 10 minutes or less, 5 minutes or less, 2 minutes or less, or 1 minute or less) after a pre-treatment vitreous sample is isolated (or, when multiple pre-treatment vitreous samples are isolated, after the final pre-treatment vitreous sample is isolated).

In some cases, more than one type of therapy may be administered to the individual. For example, a subject who has non-infectious uveitis may be treated with a glucocorticoid steroid and an antimetabolite medication such as methotrexate. A subject who has infectious uveitis may be treated with an anti-inflammatory agent after treatment with an antibiotic, antiviral agent, or antifungal agent once the infection is brought under control to reduce inflammatory damage caused by the infection.

In some embodiments, the subject methods include providing an analysis indicating whether the individual is determined to have non-infectious or infectious uveitis (and the type of infectious uveitis, e.g., bacterial, viral, or fungal). The analysis may further provide an analysis of whether an individual is responsive or not responsive to a treatment, or whether the individual is determined to be maintaining responsiveness or not maintaining responsiveness to a treatment for uveitis. As described above, an analysis can be an oral or written report (e.g., written or electronic document). The analysis can be provided to the subject, to the subject's physician, to a testing facility, etc. The analysis can also be accessible as a website address via the internet. In some such cases, the analysis can be accessible by multiple different entities (e.g., the subject, the subject's physician, a testing facility, etc.).

Detecting and Measuring Biomarkers

It is understood that the biomarkers in a sample can be measured by any suitable method known in the art. Measurement of the expression level of a biomarker can be direct or indirect. For example, the abundance levels of RNAs or proteins can be directly quantitated. Alternatively, the amount of a biomarker can be determined indirectly by measuring abundance levels of cDNAs, amplified RNAs or DNAs, or by measuring quantities or activities of RNAs, proteins, or other molecules (e.g., metabolites or metabolic byproducts) that are indicative of the expression level of the biomarker. The methods for measuring biomarkers in a sample have many applications. For example, one or more biomarkers can be measured to aid in diagnosing a patient with uveitis and determining the appropriate treatment for a subject, as well as monitoring responses of a subject to treatment.

In some embodiments, the amount or level in the sample of one or more proteins/polypeptides encoded by a gene of interest is determined. Any convenient protocol for evaluating protein levels may be employed where the level of one or more proteins in the assayed sample is determined. For antibody-based methods of protein level determination, any convenient antibody can be used that specifically binds to the intended biomarker (e.g., PGLYRP1, ELANE, MMP9, DEF1, S100A8, SPARCL1, LRP2, CNMD, CHIT1, MPO, LCN2, LCP1, CST4, CNTN1, HPD, MINP1, MMP8, CAP1, or SERPINA3). The terms "specifically binds" or "specific binding" as used herein refer to preferential binding to a molecule relative to other molecules or moieties in a solution or reaction mixture (e.g., an antibody specifically binds to a particular polypeptide or epitope relative to other available polypeptides or epitopes). In some embodiments, the affinity of one molecule for another molecule to which it specifically binds is characterized by a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). By "affinity" it is meant the strength of binding, increased binding affinity being correlated with a lower $K_d$.

While a variety of different manners of assaying for protein levels are known in the art, one representative and convenient type of protocol for assaying protein levels is the enzyme-linked immunosorbent assay (ELISA). In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is contacted with the sample to be tested under conditions that are conducive to immune complex (antigen/antibody) formation. Such conditions include diluting the sample with diluents such as BSA or bovine gamma globulin (BGG) in phosphate buffered saline (PBS)/Tween or PBS/Triton-X 100, which also tend to assist in the reduction of nonspecific background, and allowing the sample to incubate for about 2-4 hours at temperatures on the order of about 25°–27° C. (although other temperatures may be used). Following incubation, the antisera-contacted surface is washed so as to remove non-immunocomplexed material. An exemplary washing procedure includes washing with a solution such as PBS/Tween, PBS/Triton-X 100, or borate buffer. The occurrence and amount of immunocomplex formation may then be determined by subjecting the bound immunocomplexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. For example, a urease or peroxidase-conjugated anti-human IgG may be employed, for a period of time and under conditions which favor the development of immunocomplex formation (e.g., incubation for 2 hours at room temperature in a PBS-containing solution such as PBS/Tween). After such incubation with the second antibody and washing to remove unbound material, the amount of label is quantified, for example by incubation with a chromogenic substrate such as urea and bromocresol purple in the case of a urease label or 2,2'-azino-di-(3-ethyl-benzthiazoline)-6-sulfonic acid (ABTS) and $H_2O_2$, in the case of a peroxidase label. Quantitation is then achieved by measuring the degree of color generation, e.g., using a visible spectrum spectrophotometer. The preceding format may be altered by first binding the sample to the assay plate. Then, primary antibody is incubated with the assay plate, followed by detecting of bound primary antibody using a labeled second antibody with specificity for the primary antibody.

The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be effected in a manner most appropriate for the substrate being used, for example, by removing a bead or dipstick from a reservoir, emptying or diluting a reservoir such as a microtiter plate well, or rinsing a bead, particle, chromatographic column or filter with a wash solution or solvent.

Alternatively, non-ELISA based-methods for measuring the levels of one or more proteins in a sample may be employed and any convenient method may be used. Representative examples known to one of ordinary skill in the art include but are not limited to other immunoassay techniques such as radioimmunoassays (RIA), sandwich immunoassays, fluorescent immunoassays, enzyme multiplied immunoassay technique (EMIT), capillary electrophoresis immunoassays (CEIA), and immunoprecipitation assays; mass spectrometry, or tandem mass spectrometry, proteomic arrays, xMAP microsphere technology, western blotting, immunohistochemistry, flow cytometry, cytometry by time-of-flight (CyTOF), multiplexed ion beam imaging (MIBI), and detection in body fluid by electrochemical sensor. In, for example, flow cytometry methods, the quantitative level of gene products of the one or more genes of interest are detected on cells in a cell suspension by lasers. As with ELISAs and immunohistochemistry, antibodies (e.g., monoclonal antibodies) that specifically bind the polypeptides encoded by the genes of interest are used in such methods.

As another example, electrochemical sensors may be employed. In such methods, a capture aptamer or an antibody that is specific for a target protein (the "analyte") is immobilized on an electrode. A second aptamer or antibody, also specific for the target protein, is labeled with, for example, pyrroquinoline quinone glucose dehydrogenase ((PQQ)GDH). The sample of body fluid is introduced to the sensor either by submerging the electrodes in body fluid or by adding the sample fluid to a sample chamber, and the analyte allowed to interact with the labeled aptamer/antibody and the immobilized capture aptamer/antibody. Glucose is then provided to the sample, and the electric current generated by (PQQ)GDH is observed, where the amount of electric current passing through the electrochemical cell is directly related to the amount of analyte captured at the electrode.

For measuring protein activity levels, the amount or level of protein activity in the sample of one or more proteins/polypeptides encoded by the gene of interest is determined.

In other embodiments, the amount or level in the sample of one or more proteins is determined. Any convenient method for measuring protein levels in a sample may be used, e.g. antibody-based methods, e.g. immunoassays, e.g., enzyme-linked immunosorbent assays (ELISAs), immunohistochemistry, and mass spectrometry.

The resultant data provides information regarding expression, amount, and/or activity for each of the biomarkers that have been measured, wherein the information is in terms of whether or not the biomarker is present (e.g. expressed) and at what level, and wherein the data may be both qualitative and quantitative.

Data Analysis

In some embodiments, one or more pattern recognition methods can be used in analyzing the data for biomarker levels. The quantitative values may be combined in linear or non-linear fashion to calculate one or more risk scores for non-infectious or infectious uveitis for an individual. In some embodiments, measurements for a biomarker or combinations of biomarkers are formulated into linear or non-linear models or algorithms (e.g., a 'biomarker signature') and converted into a likelihood score. This likelihood score indicates the probability that a vitreous sample is from a patient who may exhibit no evidence of disease, who may exhibit non-infectious or infectious uveitis. A likelihood score can also be used to distinguish among infectious uveitis disease subtypes, including bacterial, viral, and fungal uveitis. The models and/or algorithms can be provided in machine readable format, and may be used to correlate biomarker levels or a biomarker profile with a disease state, and/or to designate a treatment modality for a patient or class of patients.

Analyzing the levels of a plurality of biomarkers may comprise the use of an algorithm or classifier. In some embodiments, a machine learning algorithm is used to classify a patient as having non-infectious or infectious uveitis or further classify the patient by an infectious uveitis subtype (e.g., bacterial, viral, or fungal uveitis). The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, temporal difference learning, 0-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

Kits

Also provided are kits for use in the methods. The subject kits include agents (e.g., an antibody that specifically binds to a biomarker and/or other immunoassay reagents, and the like) for determining the level of at least one biomarker. In some embodiments, a kit comprises agents for determining the level of a single biomarker, two or more different biomarkers, three or more different biomarkers, or all the biomarkers selected from the group consisting of PGLYRP1, ELANE, MMP9, DEF1, S100A8, SPARCL1, LRP2, CNMD, CHIT1, MPO, LCN2, LCP1, CST4, CNTN1, HPD, MINP1, MMP8, CAP1, and SERPINA3. In some embodiments, the kit comprises agents for detecting the PGLYRP1, ELANE, MMP9, DEF1, S100A8, SPARCL1, LRP2, and CNMD biomarkers for distinguishing whether a patient has non-infectious or infectious uveitis. In some embodiments, the kit comprises agents for detecting the CHIT1, MPO, LCN2, and LCP1 biomarkers for determining whether a patient has bacterial uveitis. In some embodiments, the kit comprises agents for detecting the CST4, CNTN1, HPD, and MINP1 biomarkers for determining whether a patient has viral uveitis. In some embodiments, the kit comprises agents for detecting the MMP8, CAP1, and SERPINA3 biomarkers for determining whether a patient has fungal uveitis.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), DVD, flash drive, and the like, on which the information has been recorded. Yet another form of these instructions that may be present is a website address which may be used via the internet to access the information at a removed site.

In certain embodiments, the kit further comprises reagents for performing an immunoassay. In some embodiments, the kit comprises an antibody that specifically binds to peptidoglycan recognition protein 1 (PGLYRP1), an antibody that specifically binds to elastase, neutrophil expressed (ELANE), an antibody that specifically binds to matrix metalloproteinase-9 (MMP9), an antibody that specifically binds to DNA damage-responsive RNA polymerase-degradation factor (DEF1), an antibody that specifically binds to S100 calcium binding protein A8 (S100A8), an antibody that specifically binds to SPARC like 1 protein (SPARCL1), an antibody that specifically binds to LDL receptor related protein 2 (LRP2), an antibody that specifically binds to chondromodulin (CNMD), an antibody that specifically binds to chitotriosidase-1 (CHIT1), an antibody that specifically binds to myeloperoxidase (MPO), an antibody that specifically binds to lipocalin 2 (LCN2), an antibody that specifically binds to lymphocyte cytosolic protein 1 (LCP1), an antibody that specifically binds to cystatin S (CST4), an antibody that specifically binds to contactin-1 (CNTN1), an antibody that specifically binds to 4-hydroxyphenylpyruvate dioxygenase (HPD), an antibody that specifically binds to multiple inositol polyphosphate phosphatase 1 (MINP1), an antibody that specifically binds to matrix metallopeptidase 8 (MMP8), an antibody that specifically binds to cyclase associated actin cytoskeleton regulatory protein 1 (CAP1), and an antibody that specifically binds to serpin family A member 3 (SERPINA3).

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Screening for Proteomic Biomarkers of Infectious Endophthalmitis

Introduction

Infections are one of the most common and visually devasting causes of uveitis.[1] On initial examination, it is often difficult to ascertain the infectious cause of the intraocular inflammation (bacteria, virus, fungus, helminth, or parasite). To date, the gold standard for diagnosis of infectious uveitis is a microbial culture. However, cultures are often unreliable or of low yield due to the inaccessibility to ocular fluid samples, low sample volumes, and the difficulties attributed to culturing intracellular pathogens.[1] Further, the time it takes to culture the microbial agent delays treatment, which can lead to blindness. Advancements in polymerase chain reaction (PCR) testing have improved the diagnosis of several forms of viral endophthalmitis, such as herpes simplex virus (HSV) and cytomegalovirus (CMV). However, in the case of fungal or bacterial infections, ocular tuberculosis, for example, PCR sensitivity can be as low as 37%.[1] Thus, there is a need for rapid and accurate molecular testing to differentiate the different forms of infectious uveitis.

Precision Health is inspiring a renaissance across multiple medical fields, including ophthalmology.[2] An early example of a Precision Health approach is the routine use of cardiac biomarkers for the diagnosis of myocardial infarction (MI). Despite clinical examination, a critical protein biomarker, troponin, is routinely measured as a key to diagnosis and timely intervention. Troponin assays are exquisitely sensitive to the presence of myocardial necrosis and so used to definitively diagnose acute MI.[3] In the case of organ specific diseases, sampling fluid compartments near the diseased tissue (e.g. vitreous, synovial fluid, urine, cerebral spinal fluid), may be better for diagnosing non-systemic diseases.[4-6] Vitreoretinal diseases, however, have no equivalent sensitive and specific molecular assay, leaving diagnosis and treatment most often empiric, relying heavily on findings from clinical exams.

Proteomic analysis is becoming an attractive and powerful tool for characterizing the molecular profiles of diseased tissues. The proteome of inflamed vitreous can be characterized to uncover biomarkers for specific etiologies of intraocular inflammation and infection. Our group has used large-scale proteomic platforms to analyze the protein signature in vitreous biopsies from patients with vitreoretinal disease. This approach allowed us to identify a "short list" of several candidate biomarkers that can reliably differentiate different types of uveitis (e.g. infectious, autoimmune, etc.). To advance precision health approaches for uveitis, our group has further developed and implemented a novel device and software that allows for immediate point-of-care processing of liquid biopsy specimens. A first-in-class web-based relational database for tracking phenotypes and specimens was created and used successfully in the operating room. We have shown that vitreous protein signatures can differentiate between non-infectious and infectious uveitis and determine the class of infection more rapidly than conventional clinical testing. Our approach may prevent unnecessary delays in treatment and avoid preventable blindness.

Proteomic Analysis of the Human Vitreous

Figure 2A:
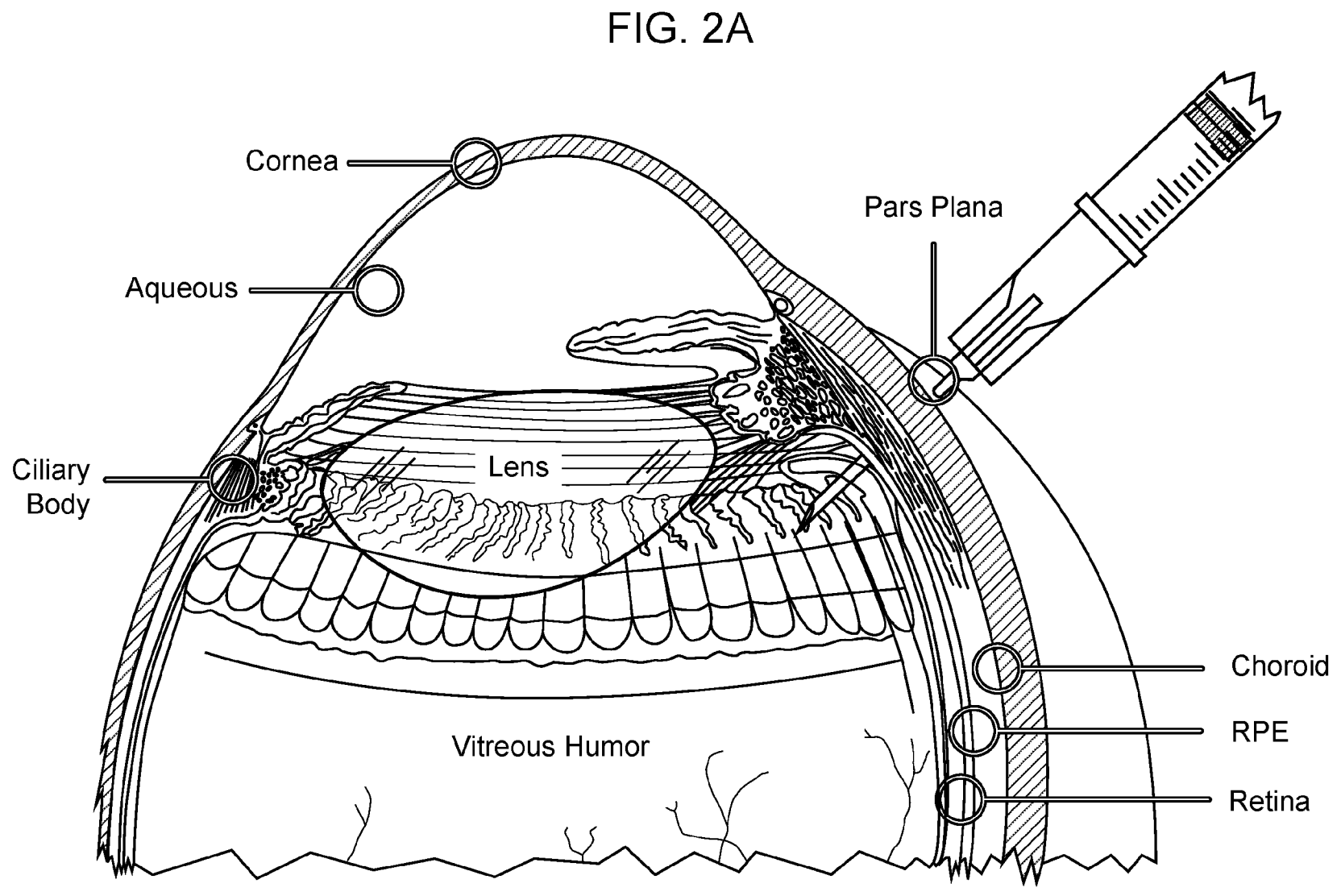

The vitreous humor is an optically-transparent extracellular matrix located in the posterior chamber of the eye, just anterior to the retina (FIG. 2A). Its composition is estimated to be 90% water, and proteomic composition varies depending on anatomic locations[8, 9] and by different vitreoretinal diseases and the different immune responses (i.e. T-cell, antibody, cytokine).[8, 17] We confirmed that damaged cells can release proteins into the vitreous[17] that otherwise go undetected in routine cell culture or PCR tests. Changes in the molecular composition of the vitreous reflect key pathologic changes during vitreoretinal disease, we have found, that correlate to disease onset, progression, and response to therapy.[10] Vitreous biopsies, primarily focused on cell composition, are used in the clinical management and diagnosis of intravitreal inflammation, infection, and cancer.[9] Proteomic analysis of liquid biopsies expands their clinical utility in the personalized management of patient care.[2, 7]

Ophthalmic Tissue Biorepository

Our group has developed a biorepository and personalized proteomics pipeline for ophthalmic surgical specimens. Patients are screened for any acute or chronic disease prior to enrollment. Patients undergo full ophthalmic examination and laboratory testing that may include Fluorescein angiographic, Goldmann visual field, complete blood cell count, erythrocyte sedimentation rate, levels of C-reactive protein, antinuclear antibody, rheumatoid factor, interferon-γ release, HLA-B27, titers for Lyme disease, hepatitis B virus antibody, and hepatitis C surface antigen. Vitreous biopsies are obtained from living patients by fine needle aspiration (FNA) or pars plana vitrectomy (PPV) in the operating room.[9, 11] Proper care and handling of biopsy specimens is critical to quality control for subsequent proteomic analysis.[12] To ensure tissues are immediately cataloged, processed, and stored, we developed the mobile operating room lab interface (MORLI).[12] The MORLI system has several key components: a mobile operating-room cart with a lab-bench surface, a computer with secure access to a sample database, a barcode scanner, and drawers with lab supplies for specimen collection (e.g., pipettors, centrifuge, dissecting microscope, cryotubes, and a small liquid nitrogen dewar). The MORLI cart allows samples to be processed away from the surgical field.

Figure 2B:
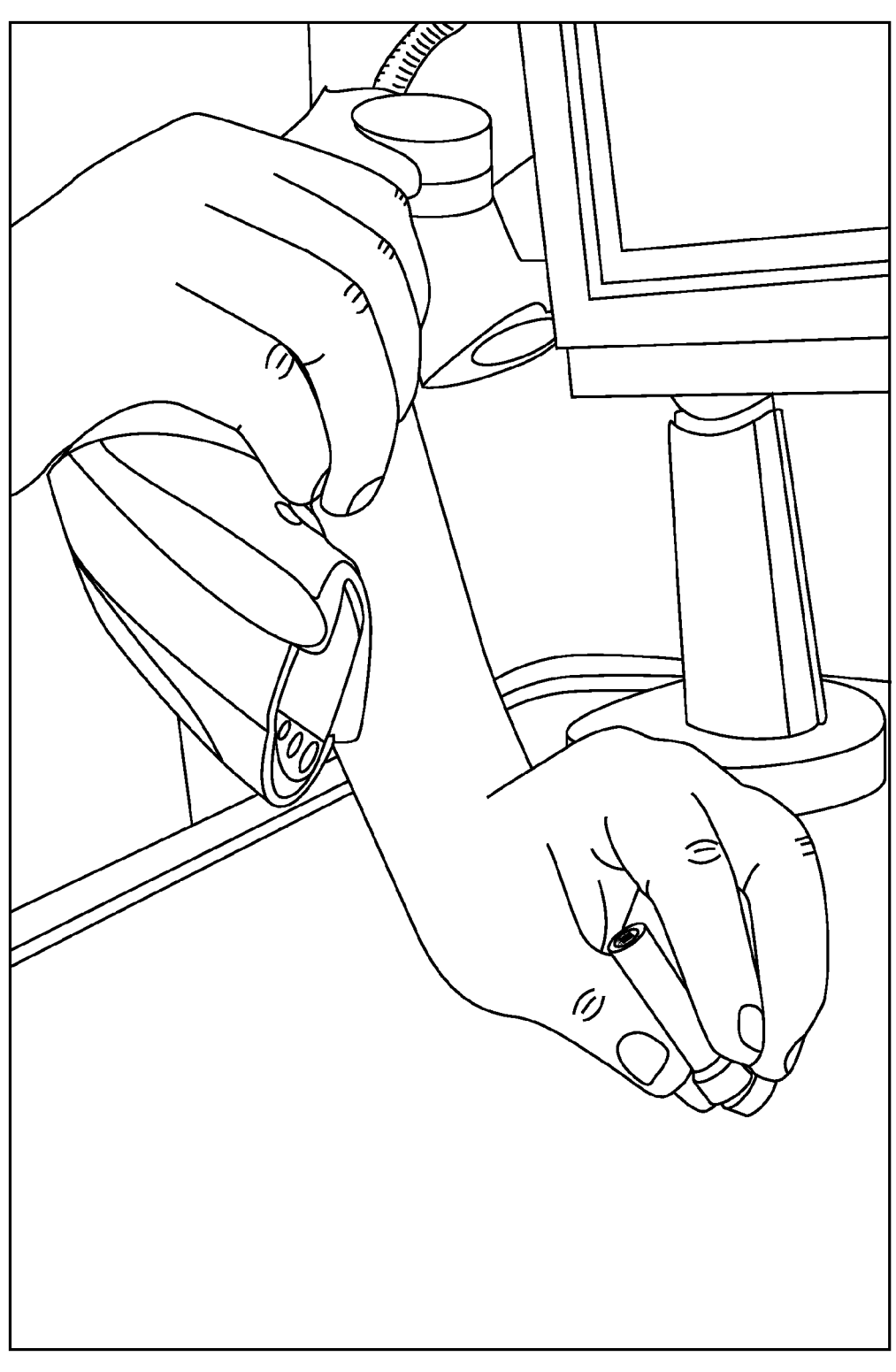
Figure 2C:
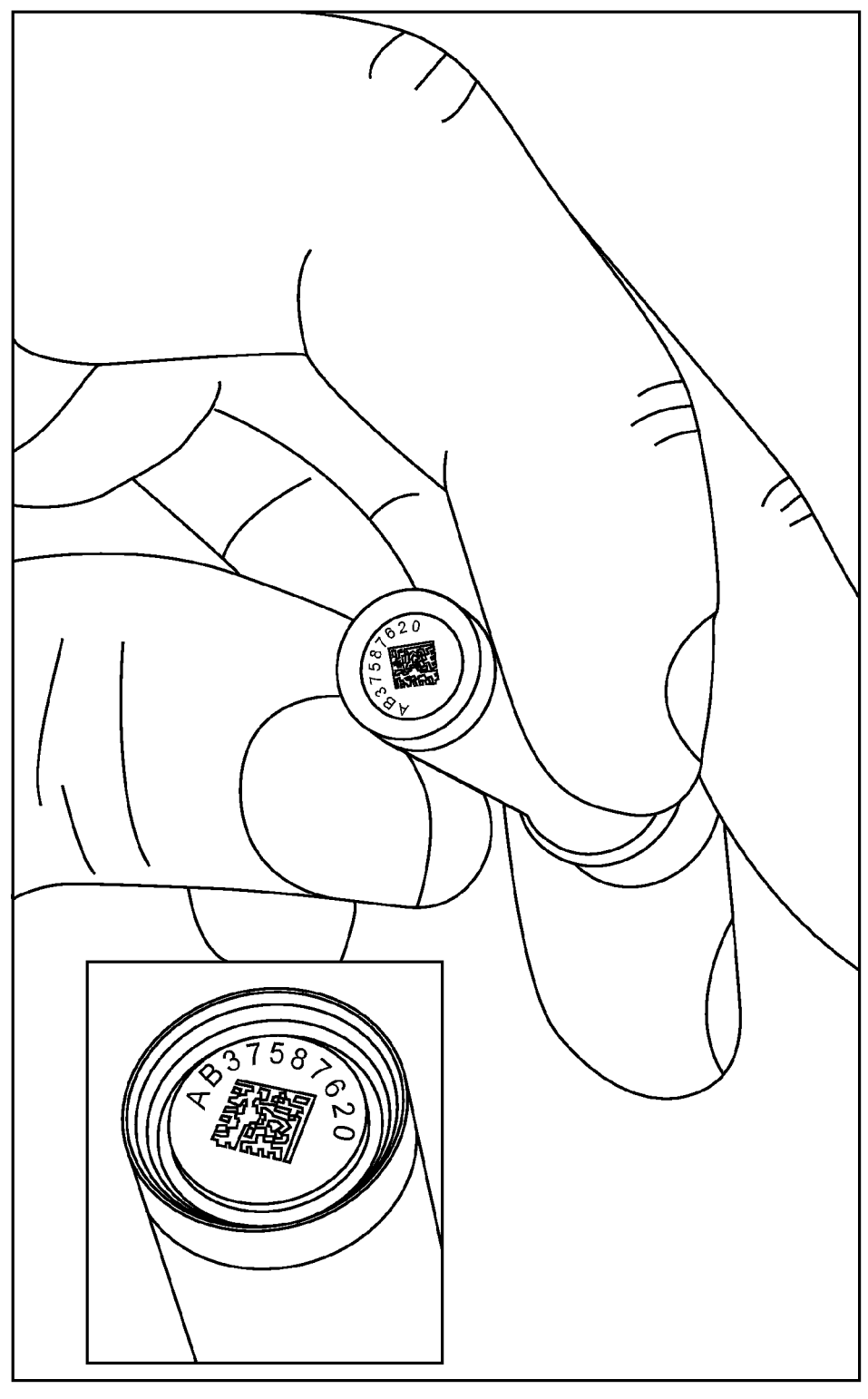
Figure 2D:
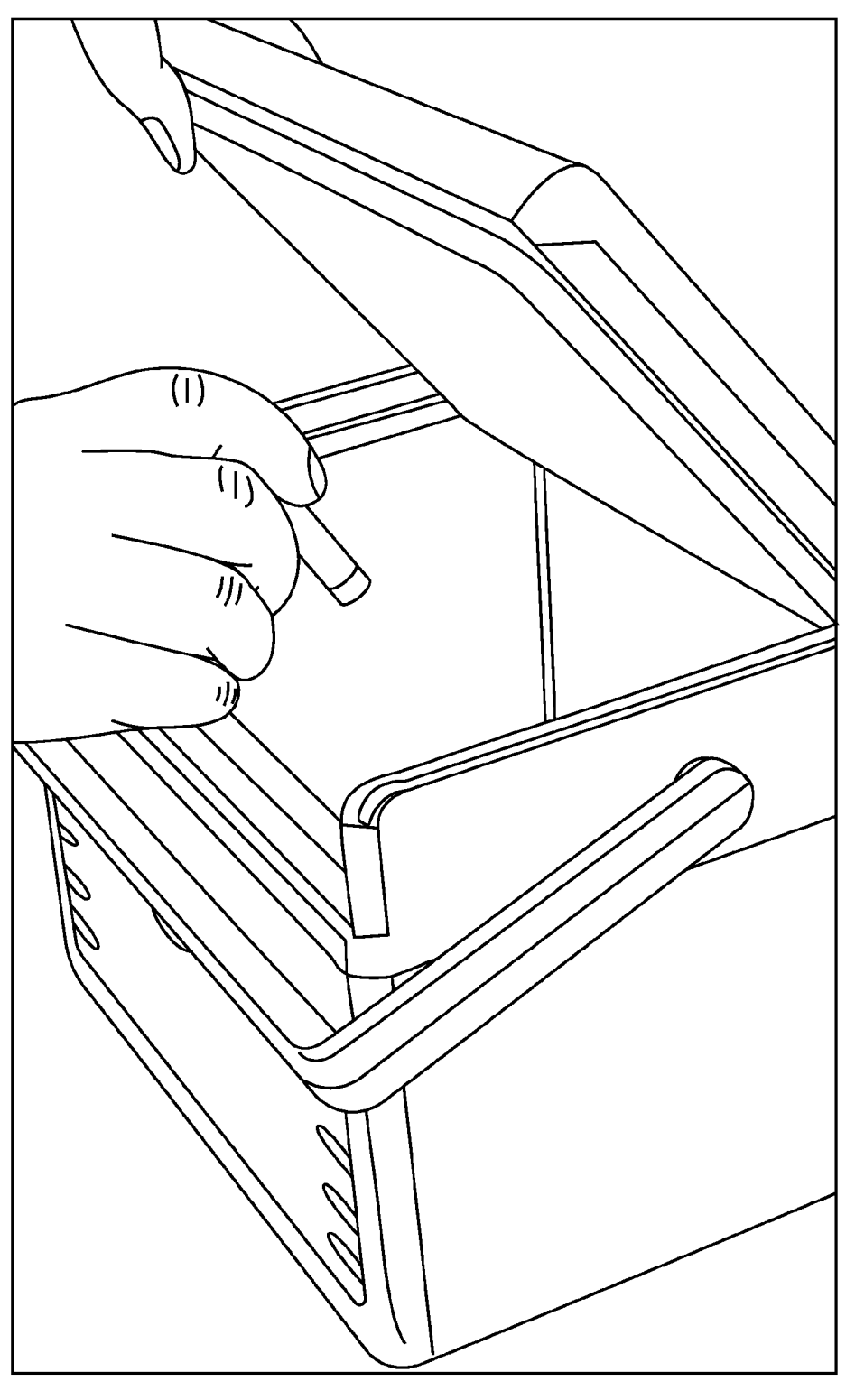

Over 1000 liquid vitreous samples were transferred to a barcoded cryotube, and flash-frozen in liquid nitrogen. The corresponding sample barcode was entered into a custom electronic relational database (MySQL) for efficient sample logging and retrieval,[12] and is also linked to patient retrospective and prospective clinical data (IRB approved). This biorepository system streamlined our personalized proteomics pipeline for the study of ophthalmic diseases (FIGS. 2B-2D). Once surgical specimens are properly collected, processed, and stored, their proteomic composition can be analyzed and associated with patient clinical information.

Infectious endophthalmitis proteomes are analyzed exclusively from culture (bacterial, fungal) and PCR-positive (viral) vitreous samples. Our patient samples are roughly 50% male and 50% female. Samples are analyzed both as a group and separated by sex.

Example 2

Protein Signatures that Distinguish between Infectious and Non-infectious Uveitis Posterior uveitis has high morbidity because the retina is intolerant of immunologic insult. The etiology for over 50% of posterior uveitis cases is not known and these cases are thus labeled as "idiopathic," thereby delaying targeting of the inciting agent. An initial diagnostic hurdle is determining whether the cause of inflammation is due to an infection (endophthalmitis) or an autoimmune response.

We performed a shotgun proteomics screen for candidate vitreous biomarkers of infectious endophthalmitis. Vitreous samples were collected from infectious endophthalmitis patients, non-infectious uveitis (retained lens uveitis), and non-inflammatory controls (with either epiretinal membranes or macular holes). Proteins were extracted from vitreous (20 µg protein per sample), precipitated in chloroform-methanol, dissolved in 0.1% Rapigest detergent in 50 mM ammonium bicarbonate, and digested by trypsin (1:40 protease: protein ratio). Mass spectrometry-based measurements were performed in duplicate for control and uveitis vitreous samples. A liquid chromatography-tandem mass spectrometry (LC-MS/MS) approach was used for the relative quantitation and simultaneous identification of proteins. We used a Q Exactive HF Hybrid Quadrupole-Orbitrap mass spectrometer (Thermo Fisher). Data-independent acquisition (DIA) was used to generate MS data within a 25 Da fixed window. Positive identification was set at 1% peptide FDR. The sum of all MS2 area under the curve (AUC) from peptides assigned to each protein was used for quantitation. K-Nearest Neighbor (KNN) imputation was used for missing values.

Figure 3A:
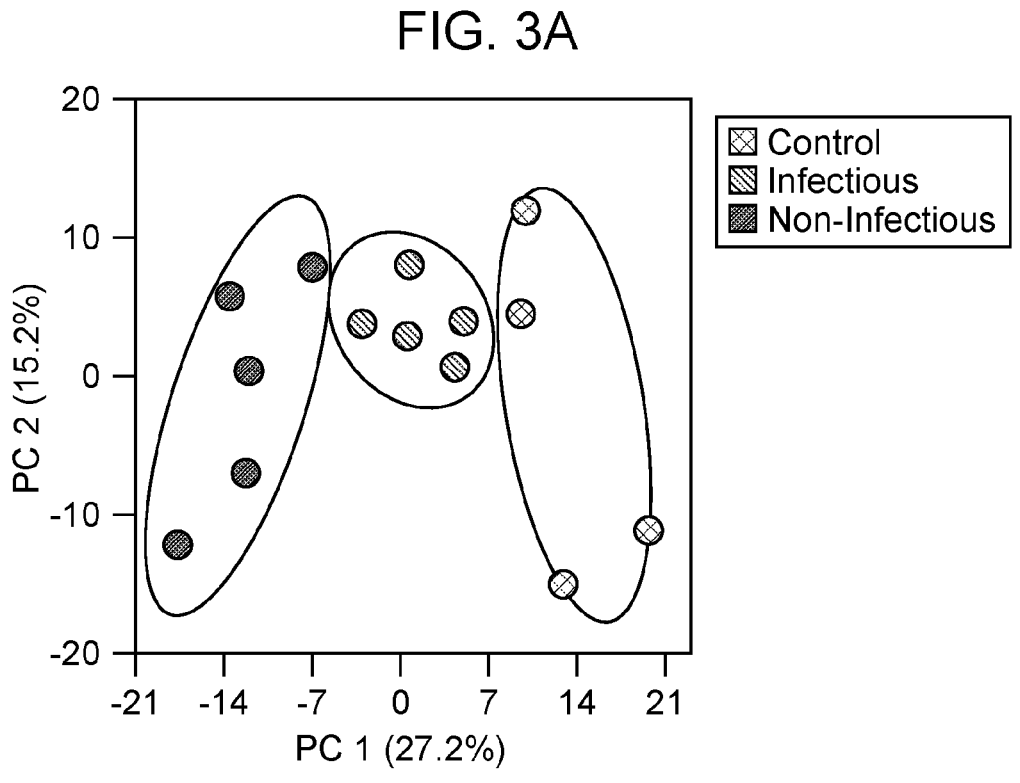
FIGS. 3A-3B show proteomic profiles differ between infectious and non-infectious uveitis.
Figure 3B:
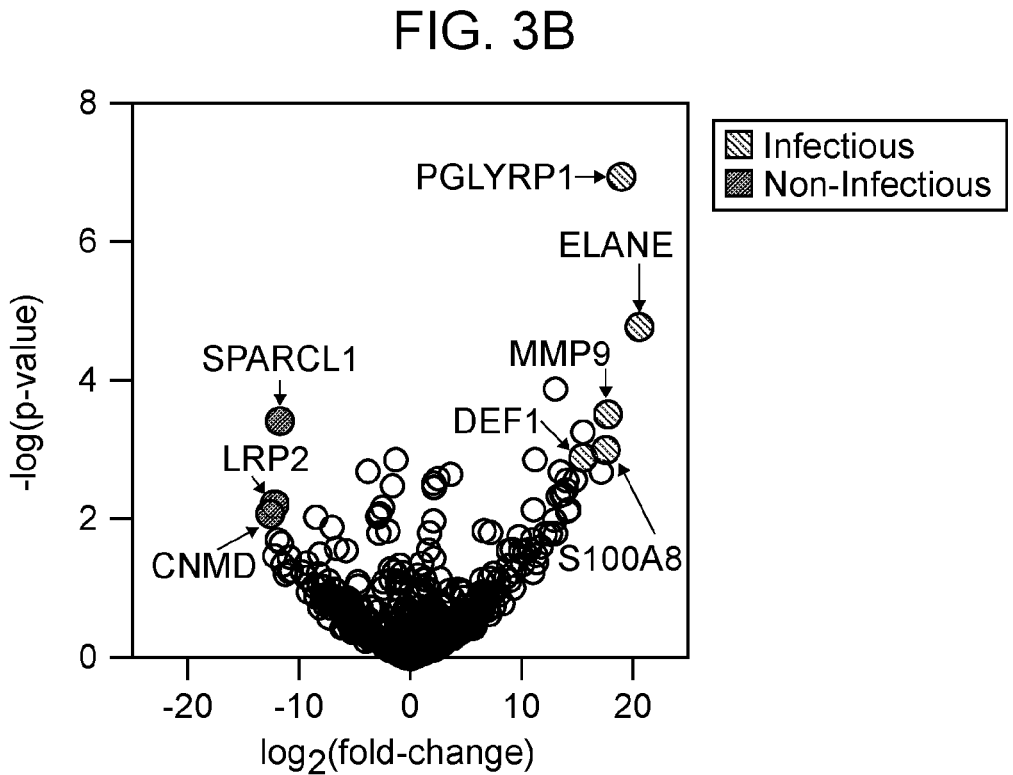

Proteomics data were then compared using principal component analysis (PCA). The score plot of PC1 and PC2 showed separation between the 5 non-infectious uveitis cases, 5 infectious endophthalmitis cases, and 4 controls based on the protein intensities that were significantly different between the three groups (FIG. 3A). Protein intensities were analyzed with 1-way ANOVA. There were 77 differentially-expressed proteins between infectious uveitis vs. non-infectious uveitis cases (p<0.05), providing an excellent reference for potential biomarkers for infectious endophthalmitis (FIG. 3B). The most significantly upregulated proteins in infectious endophthalmitis were: peptidoglycan recognition protein 1 (PGLYRP1), neutrophil elastase (ELANE), neutrophil defensin 1 (DEF1), matrix metalloprotease 9 (MMP9), and protein S100-A8 (S100A8; Table 1). The most significantly upregulated proteins in non-infectious uveitis were: SPARC-like protein 1 (SPARCL1), low-density lipoprotein receptor-related protein 2 (LRP2), and leukocyte cell-derived chemotaxin 1 (CNMD; Table 1).

Example 3

Proteomic Biomarkers for Different Classes of Infectious Endophthalmitis:

There are few rapid and reliable diagnostic options for infectious endophthalmitis. Patients are broadly treated due to the low yield of Gram stains and culture.[1] Our working hypothesis was that specific etiologies of infectious endophthalmitis (e.g., bacterial, viral, fungal, and parasitic) can be differentiated by specific protein biomarkers, since they elicit different immune responses.

Our mass spectrometry-based screen identified characteristic protein signatures associated with specific infectious types of endophthalmitis. Candidate biomarkers are shown in Table 3. Vitreous samples from patients with bacterial, viral, and fungal endophthalmitis were separately compared to controls using 1-way ANOVA and hierarchical heatmap clustering. Lists of upregulated proteins from each infection class (p<0.05) were then compared using Venn diagram analysis (FIG. 4B). This comparative analysis identified protein signatures and biomarkers unique for bacterial endophthalmitis: chitotriosidase-1 (CHIT1), myeloperoxidase (MPO), neutrophil gelatinase-associated lipocalin (LCN2), and plastin-2 (LCP1); viral endophthalmitis: cystatin-S(CST4), contactin-1 (CNTN1), 4-hydroxyphenylpyurvate dioxygenase (HPD), and multiple inositol polyphosphate phosphatase 1 (MINP1); and fungal endophthalmitis: neutrophil elastase (MMPB), adenylyl cyclase-associated protein 1 (CAP1) and alpha-1-antichymotrypsin (SERPINA3; Table 3).

Figure 4A:
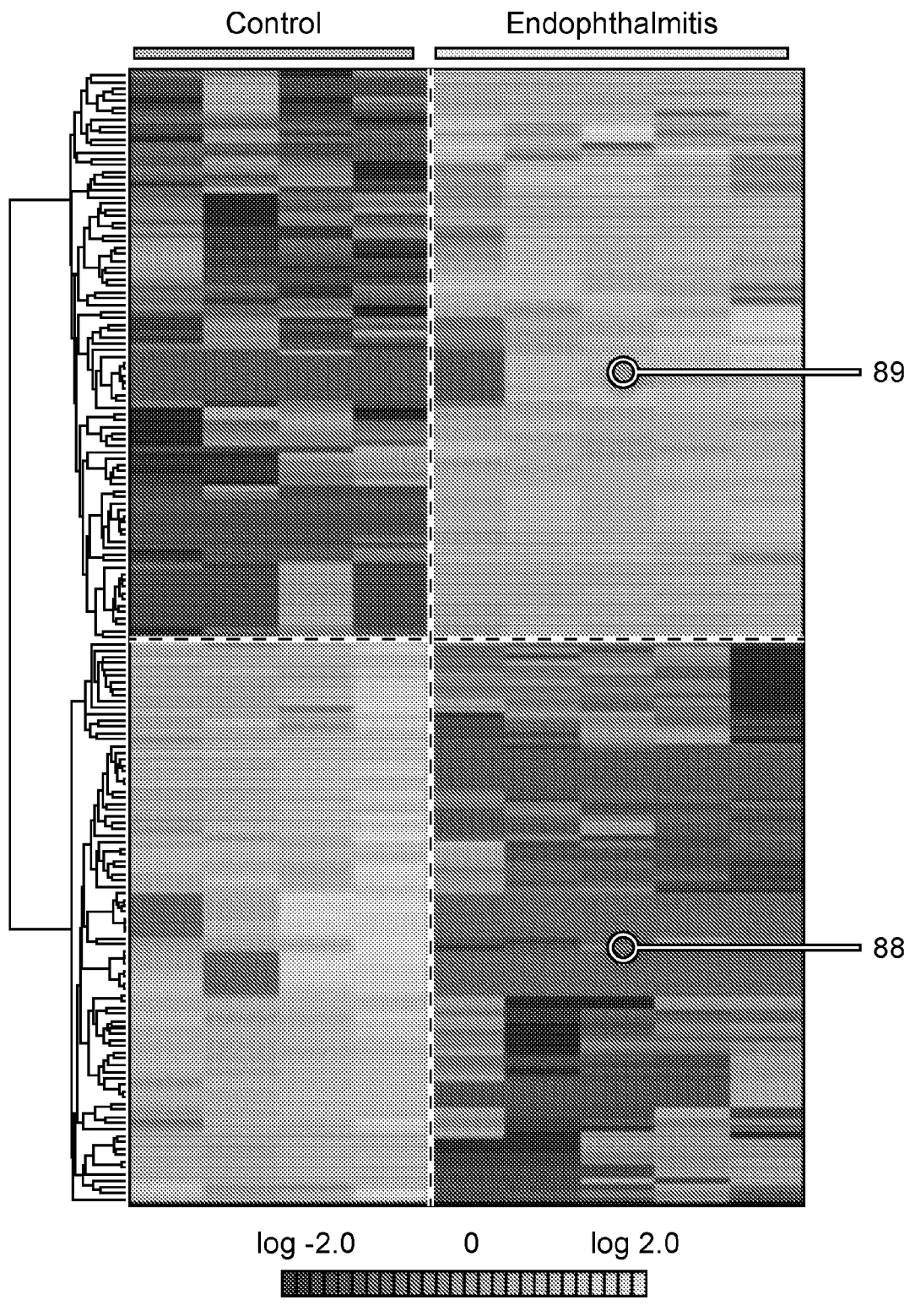
FIGS. 4A-4B show that proteomic profiles differ between classes of infectious endophthalmitis.
Figure 4B:
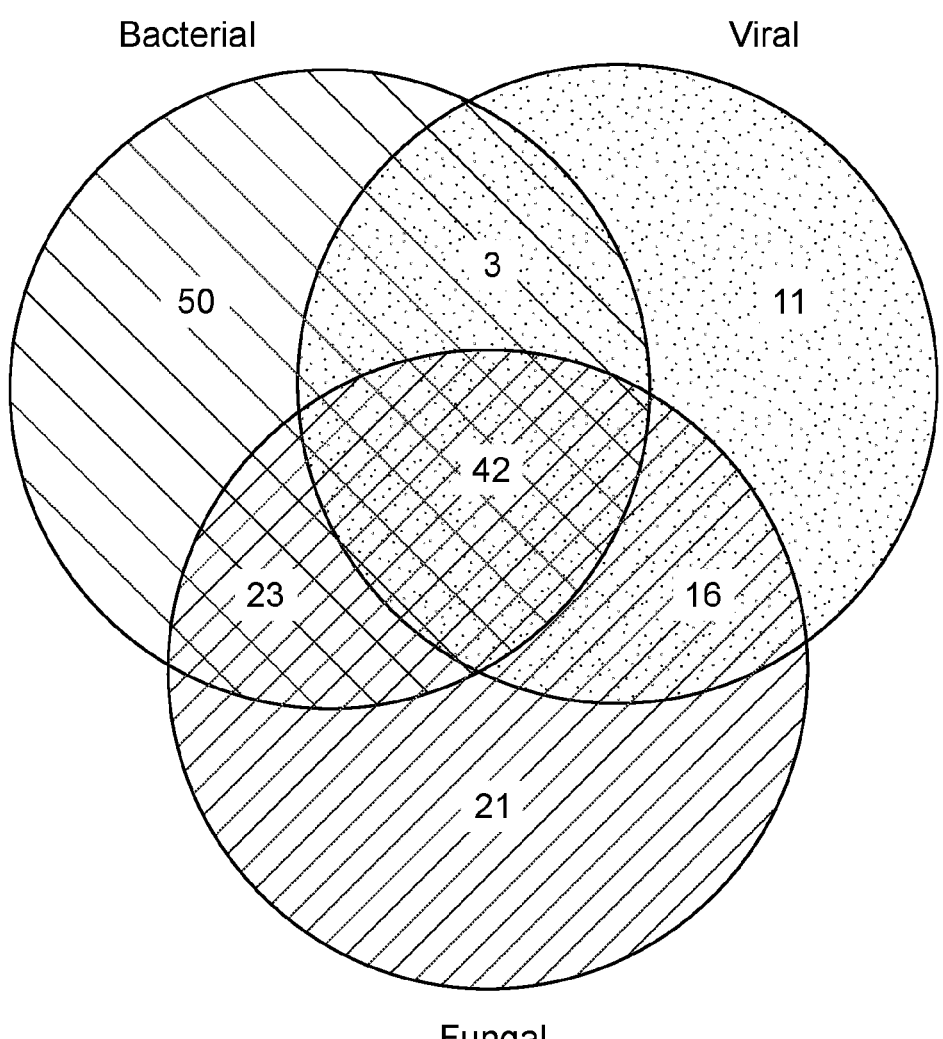

Mass-spec protein intensity levels were analyzed using 1-way ANOVA (FIG. 4A). The proteins that had the highest fold-change in endophthalmitis vitreous compared to controls were neutrophil gelatinase-associated lipocalin (LCN2), neutrophil elastase (ELANE), neutrophil defensin 1 (DEF1), and cathelicidin anti-microbial peptide (CAMP; FIG. 4A). In particular, CAMP is an extracellular antimicrobial protein that binds to bacterial lipopolysaccharides (LPS) and displays a 1.5 million-fold increase in bacterial endophthalmitis vitreous compared to controls and infection cases due to virus or fungus.[19] These specific proteomic biomarkers can distinguish among different classes of infectious endophthalmitis including bacterial, viral, and fungal endophthalmitis and can be readily measured in vitreous biopsies using a custom multiplex ELISA array.

Example 4

Statistical Analysis

For quantitative proteomics, the pwr.2p.test( ) function in the R statistical software package is a standard in the field that calculates theoretical cut-offs that can be used in quantitative analyses as a function of sample size.[20] Given an average variation in protein expression, the pwr.2p.test( ) function predicts the number of biological replicates required for a given fold-change in protein expression. For example, an analysis that includes a sample size of 4 (and 40% total variation), the minimum difference required with a power of 80% is a four-fold change in protein expression. Power can also be calculated retrospectively for a given list of proteins using their p-value, variation, fold-change, and sample size. Our total sample size (of >1,000 cases) is sufficient to detect fold-changes as low as 1.5-fold with a total variation of 40%. Experiments are performed with the tester masked to diagnosis.

Example 5

Diagnostic Screening for Biomarkers by ELISA

Candidate biomarkers (Table 1) are measured in vitreous samples using a custom multiplex ELISA array per the manufacturer's protocol (RayBio, Norcross, Ga.). This array concurrently detects and processes levels of protein biomarkers. Proteins present at a level of 500 pg/mL or higher are selected for further evaluation. This cut-off was chosen because it is higher than the assay sensitivity (500 pg/mL), but low enough to catch all significantly-expressed proteins, while removing any under-expressed or unexpressed proteins. Numerous controls are utilized to determine protein signatures and pathways specific to infectious etiologies of intraocular inflammation (Table 2).

The linearity and reproducibility of our ELISA measurements have been confirmed in our training datasets (data not shown). ELISA results are analyzed by rigorous statistical methods: Protein expression is analyzed by 1-way ANOVA with stringent multiple test corrections (Bonferroni correction and p-value adjustments for multiplicity) followed by hierarchical clustering.

REFERENCES

1. Lin P. Infectious Uveitis. Curr Ophthalmol Rep. 2015; 3(3):170-83. Epub 2015/12/01. doi: 10.1007/s40135-015-0076-6. PubMed PMID: 26618074; PMCID: PMC4659396.
2. Velez G, Tang P H, Cabral T, Cho G Y, Machlab D A, Tsang S H, Bassuk A G, Mahajan V B. Personalized Proteomics for Precision Health: Identifying Biomarkers of Vitreoretinal Disease. Transl Vis Sci Technol. 2018; 7(5):12. doi: 10.1167/tvst.7.5.12. PubMed PMID: 30271679; PMCID: PMC6159735.
3. Daubert M A, Jeremias A. The utility of troponin measurement to detect myocardial infarction: review of the current findings. Vasc Health Risk Manag. 2010; 6:691-9. Epub 2010/09/23. PubMed PMID: 20859540; PMCID: PMC2941782.
4. Shankar G M, Balaj L, Stott S L, Nahed B, Carter B S. Liquid biopsy for brain tumors. Expert Rev Mol Diagn. 2017; 17(10):943-7. Epub 2017/09/07. doi: 10.1080/14737159.2017.1374854. PubMed PMID: 28875730; PMCID: PMC5856481.
5. Di Meo A, Bartlett J, Cheng Y, Pasic M D, Yousef G M. Liquid biopsy: a step forward towards precision medicine in urologic malignancies. Mol Cancer. 2017; 16(1):80. Epub 2017/04/16. doi: 10.1186/s12943-017-0644-5. PubMed PMID: 28410618; PMCID: PMC5391592.
6. Rosengren S, Firestein G S, Boyle D L. Measurement of inflammatory biomarkers in synovial tissue extracts by enzyme-linked immunosorbent assay. Clin Diagn Lab Immunol. 2003; 10(6):1002-10. Epub 2003/11/11. PubMed PMID: 14607859; PMCID: PMC262451.
7. Velez G, Roybal C N, Colgan D, Tsang S H, Bassuk A G, Mahajan V B. Precision Medicine: Personalized Proteomics for the Diagnosis and Treatment of Idiopathic Inflammatory Disease. JAMA Ophthalmol.

2016; 134(4):444-8. doi: 10.1001/jamaophthal-mol.2015.5934. PubMed PMID: 26848019; PMCID: PMC4833518.

8. Le Goff M M, Bishop P N. Adult vitreous structure and postnatal changes. Eye (Lond). 2008; 22(10):1214-22. Epub 2008/03/01. doi: 10.1038/eye.2008.21. PubMed PMID: 18309340.

9. Skeie J M, Brown E N, Martinez H D, Russell S R, Birkholz E S, Folk J C, Boldt H C, Gehrs K M, Stone E M, Wright M E, Mahajan V B. Proteomic analysis of vitreous biopsy techniques. Retina. 2012; 32(10):2141-9. Epub 2012/10/26. doi: 10.1097/IAE.0b013e3182562017. PubMed PMID: 23095728; PMCID: PMC3637028.

10. Velez G, Bassuk A G, Colgan D, Tsang S H, Mahajan V B. Therapeutic drug repositioning using personalized proteomics of liquid biopsies. JCI Insight. 2017; 2(24). doi: 10.1172/jci.insight.97818. PubMed PMID: 29263305; PMCID: PMC5752263.

11. Mahajan V B, Skeie J M. Translational vitreous proteomics. Proteomics Clin Appl. 2014; 8(3-4):204-8. Epub 2013/10/12. doi: 10.1002/prca.201300062. PubMed PMID: 24115652; PMCID: PMC3964148.

12. Skeie J M, Tsang S H, Zande R V, Fickbohm M M, Shah S S, Vallone J G, Mahajan V B. A biorepository for ophthalmic surgical specimens. Proteomics Clin Appl. 2014; 8(3-4):209-17. Epub 2013/10/12. doi: 10.1002/prca.201300043. PubMed PMID: 24115637; PMCID: PMC3964151.

13. Machlab D A, Velez G, Bassuk A G, Mahajan V B. ProSave: an application for restoring quantitative data to manipulated subsets of protein lists. Source Code Biol Med. 2018; 13:3. doi: 10.1186/s13029-018-0070-0. PubMed PMID: 30459825; PMCID: PMC6233572.

14. Roybal C N, Velez G, Toral M A, Tsang S H, Bassuk A G, Mahajan V B. Personalized Proteomics in Proliferative Vitreoretinopathy Implicate Hematopoietic Cell Recruitment and mTOR as a Therapeutic Target. Am J Ophthalmol. 2018; 186:152-63. doi: 10.1016/j.ajo.2017.11.025. PubMed PMID: 29246578; PMCID: PMC5805631.

15. Velez G, Machlab D A, Tang P H, Sun Y, Tsang S H, Bassuk A G, Mahajan V B. Proteomic analysis of the human retina reveals region-specific susceptibilities to metabolic- and oxidative stress-related diseases. PLoS One. 2018; 13(2):e0193250. doi: 10.1371/journal.pone.0193250. PubMed PMID: 29466423; PMCID: PMC5821407.

16. Velez G, Roybal C N, Binkley E, Bassuk A G, Tsang S H, Mahajan V B. Proteomic Analysis of Elevated Intraocular Pressure with Retinal Detachment. Am J Ophthalmol Case Rep. 2017; 5:107-10. doi: 10.1016/j.ajoc.2016.12.023. PubMed PMID: 28825049; PMCID: PMC5560621.

17. Piehowski P D, Petyuk V A, Orton D J, Xie F, Moore R J, Ramirez-Restrepo M, Engel A, Lieberman A P, Albin R L, Camp D G, Smith R D, Myers A J. Sources of technical variability in quantitative LC-MS proteomics: human brain tissue sample analysis. J Proteome Res. 2013; 12(5):2128-37. doi: 10.1021/pr301146m. PubMed PMID: 23495885; PMCID: PMC3695475.

18. Steffen P, Krisp C, Yi W, Yang P, Molloy M P, Schluter H. Multi-laboratory analysis of the variability of shipped samples for proteomics following non-cooled international transport. Anal Biochem. 2018; 548:60-5. doi: 10.1016/j.ab.2018.02.026. PubMed PMID: 29486204.

19. Kosciuczuk E M, Lisowski P, Jarczak J, Strzalkowska N, Jozwik A, Horbanczuk J, Krzyzewski J, Zwierzchowski L, Bagnicka E. Cathelicidins: family of antimicrobial peptides. A review. Mol Biol Rep. 2012; 39(12):10957-70. doi: 10.1007/s11033-012-1997-x. PubMed PMID: 23065264; PMCID: PMC3487008.

20. Levin Y. The role of statistical power analysis in quantitative proteomics. Proteomics. 2011; 11(12):2565-7. doi: 10.1002/pmic.201100033. PubMed PMID: 21591257.

TABLE 1

| Candidate Biomarkers | | | | |
| --- | --- | --- | --- | --- |
| Biomarker | Condition | GO - Biological Process | Fold-change | p-value |
| PGLYRP1 | Infectious | Antimicrobial humoral response | $5.53 \times 10^{5*}$ | $1.08 \times 10^{-7}$ |
| ELANE | Infectious | Antimicrobial humoral response | $1.59 \times 10^{6*}$ | $1.71 \times 10^{-5}$ |
| MMP9 | Infectious | Metallopeptidase activity | $2.25 \times 10^{5*}$ | $2.99 \times 10^{-4}$ |
| DEF1 | Infectious | Antimicrobial humoral response | $2.19 \times 10^{4*}$ | $9.34 \times 10^{-4}$ |
| S100A8 | Infectious | Antimicrobial humoral response | $4.99 \times 10^{4*}$ | $1.32 \times 10^{-3}$ |
| SPARCL1 | Non-Infectious | Synaptic membrane adhesion | $-3.43 \times 10^{4\dagger}$ | $3.73 \times 10^{-4}$ |
| LRP2 | Non-Infectious | Receptor, endocytosis | $-6.23 \times 10^{4\dagger}$ | $8.09 \times 10^{-3}$ |
| CNMD | Non-Infectious | Chemotaxis | $-5.64 \times 10^{2\dagger}$ | $2.50 \times 10^{-2}$ |

*upregulated compared to non-infectious uveitis;
†downregulated compared to infectious uveitis

TABLE 2

| Experimental Conditions and Controls | | |
| --- | --- | --- |
| Condition | Purpose | Description |
| Epiretinal Membrane | Negative control | Non-inflammatory control |
| Macular Hole | Negative control | Non-inflammatory control |
| Retained Lens Uveitis | Negative control | Inflammatory, non-infectious control |
| Sterile Endophthalmitis | Negative control | Inflammatory, non-infectious control |

TABLE 2-continued

| Experimental Conditions and Controls | | |
|---|---|---|
| Condition | Purpose | Description |
| Sarcoidosis | Negative control | Differential diagnosis |
| Retinal Detachment | Negative control | Inflammatory, non-infectious control |
| Diabetic Retinopathy | Negative control | Inflammatory, non-infectious control |
| Bacterial Endophthalmitis | Experimental | Culture-positive bacterial endophthalmitis |
| Viral Endophthalmitis | Experimental | PCR-confirmed viral endophthalmitis |
| Fungal Endophthalmitis | Experimental | Culture-positive fungal endophthalmitis |
| Tuberculosis Uveitis | Positive control | Infectious positive control |

TABLE 3

| Candidate Biomarkers | | | | |
|---|---|---|---|---|
| Biomarker | Infection Class | GO - Biological Process | Fold-change* | p-value |
| CAMP | All | Antimicrobial humoral response | $5.72 \times 10^7$ | $5.76 \times 10^{-7}$ |
| CHIT1 | Bacterial | Response to bacterium | $1.57 \times 10^5$ | $1.81 \times 10^{-2}$ |
| MPO | Bacterial | Response to bacterium | $8.27 \times 10^6$ | $2.45 \times 10^{-2}$ |
| LCN2 | Bacterial | Response to lipopolysaccharide | $1.37 \times 10^8$ | $2.02 \times 10^{-2}$ |
| LCP1 | Bacterial | T-cell activation | $6.59 \times 10^3$ | $4.30 \times 10^{-2}$ |
| CST4 | Viral | Retinal homeostasis | $1.63 \times 10^6$ | $2.21 \times 10^{-3}$ |
| CNTN1 | Viral | Cell adhesion | $4.13 \times 10^8$ | $7.57 \times 10^{-3}$ |
| HPD | Viral | Amino acid metabolism | $1.23 \times 10^7$ | $1.49 \times 10^{-24}$ |
| MINP1 | Viral | Metabolic process | $1.86 \times 10^2$ | $4.41 \times 10^{-2}$ |
| MMP8 | Fungal | Metalloprotease activity | $5.35 \times 10^4$ | $1.25 \times 10^{-24}$ |
| CAP1 | Fungal | Ameboid-type cell migration | $7.10 \times 10^3$ | $1.33 \times 10^{-24}$ |
| SERPINA3 | Fungal | Acute phase response | $6.82 \times 10^0$ | $1.62 \times 10^{-2}$ |

*upregulated compared to non-inflammatory controls

What is claimed is:

1. A method of diagnosing and treating uveitis in a patient, the method comprising:

a) obtaining a vitreous sample from an eye of the patient;

b) measuring levels of expression of at least 3 biomarkers selected from the group consisting of peptidoglycan recognition protein 1 (PGLYRP1), elastase, neutrophil expressed (ELANE), matrix metalloproteinase-9 (MMP9), DNA damage-responsive RNA polymerase-degradation factor (DEF1), S100 calcium binding protein A8 (S100A8), SPARC like 1 protein (SPARCL1), LDL receptor related protein 2 (LRP2), and chondromodulin (CNMD) in the vitreous sample;

c) diagnosing the patient with infectious uveitis or non-infectious uveitis, wherein increased levels of expression of PGLYRP1, ELANE, MMP9, DEF1, and S100A8 compared to reference value ranges for a vitreous sample from a subject having non-infectious uveitis indicate that the patient has infectious uveitis, and decreased levels of expression of SPARCL1, LRP2, and CNMD compared to reference value ranges for a vitreous sample from a subject having infectious uveitis indicate that the patient has non-infectious uveitis; and d) administering a glucocorticoid steroid, a cycloplegic agent, an antimetabolite, a T-cell inhibitor, an anti-tumor necrosis factor (TNF) agent, a biologic agent, or an alkylating agent to the patient diagnosed with non-infectious uveitis.

2. The method of claim 1, further comprising:

measuring levels of expression of chitotriosidase-1 (CHIT1), myeloperoxidase (MPO), lipocalin 2 (LCN2), and lymphocyte cytosolic protein 1 (LCP1) in the vitreous sample if the patient has a positive diagnosis for infectious uveitis;

diagnosing the patient with bacterial uveitis when increased levels of expression of CHIT1, MPO, LCN2, and LCP1 relative to reference value ranges for a control vitreous sample from an uninfected subject indicate that the patient has bacterial uveitis; and administering an antibiotic to the patient diagnosed with bacterial uveitis.

3. The method of claim 2, wherein the antibiotic is selected from the group consisting of cephalosporins, vancomycin, ceftazidime, amikacin, gentamycin, and moxifloxacin.

4. The method of claim 1, further comprising:

measuring levels of expression of CST4, CNTN1, HPD, and MINP1 in the vitreous sample if the patient has a positive diagnosis for infectious uveitis;

diagnosing the patient with viral uveitis when increased levels of expression of cystatin S (CST4), contactin-1 (CNTN1), 4-hydroxyphenylpyruvate dioxygenase (HPD), and multiple inositol polyphosphate phosphatase 1 (MINP1) relative to reference value ranges for a control vitreous sample from an uninfected subject indicate that the patient has viral uveitis; and administering an antiviral agent to the patient diagnosed with viral uveitis.

5. The method of claim 4, wherein the antiviral agent is selected from the group consisting of ganciclovir, acyclovir, foscarnet, valacyclovir, and cidofivir.

6. The method of claim 1, further comprising:

measuring levels of expression of matrix metallopeptidase 8 (MMP8), cyclase associated actin cytoskeleton regulatory protein 1 (CAP1), and serpin family A member 3 (SERPINA3) in the vitreous sample;

diagnosing the patient with fungal uveitis when increased levels of expression of MMP8, CAP1, and SERPINA3 relative to reference value ranges for a control vitreous sample from an uninfected subject indicate that the patient has fungal uveitis; and administering an antifungal agent to the patient diagnosed with fungal uveitis.

7. The method of claim 6, wherein the antifungal agent is selected from the group consisting of amphotericin B, voriconazole, caspofungin, and fluconazole.

8. The method of claim 1, wherein said treating further comprises performing a vitrectomy.

9. The method of claim 1, wherein said measuring the levels of expression comprises performing mass spectrometry, tandem mass spectrometry, an enzymatic or biochemical assay, liquid chromatography, nuclear magnetic resonance (NMR), an enzyme-linked immunosorbent assay (ELISA), a radioimmunoassay (RIA), an immunofluorescent assay (IFA), immunohistochemistry, fluorescence-activated cell sorting (FACS), or a Western Blot.

10. The method of claim 9, wherein the ELISA is performed using a multiplex ELISA array.

\* \* \* \* \*